United States Patent [19]

Okuno et al.

[11] Patent Number: 5,684,146

[45] Date of Patent: Nov. 4, 1997

[54] DNA CODING FOR VARIABLE REGION TO HUMAN INFLUENZA A TYPE VIRUS

[75] Inventors: Yoshinobu Okuno, Toyonaka; Atsushi Oshima, Otsu; Hirofumi Yoshioka, Shiga-ken; Takashi Takabatake, Nagoya; Ikunoshin Kato, Uji, all of Japan

[73] Assignee: Takara Shuzo Co., Ltd., Kyoto-fu, Japan

[21] Appl. No.: 401,908

[22] Filed: Mar. 10, 1995

[30] Foreign Application Priority Data

Mar. 30, 1994 [JP] Japan ..................................... 6-082693

[51] Int. Cl.⁶ .............................. C12N 15/13; C12N 5/12; C07H 21/04; C07K 16/08
[52] U.S. Cl. .................................. 536/23.53; 530/387.1; 530/388.3; 435/339; 435/320.1
[58] Field of Search ..................... 536/235.3; 530/387.1, 530/388.3; 435/240.27, 240.2, 320.1, 339

[56] References Cited

U.S. PATENT DOCUMENTS 5,318,897  6/1994  Paul ........................................ 435/68.1

FOREIGN PATENT DOCUMENTS

| 0 621 339 A3 | 10/1994 | European Pat. Off. . |
| 115216 | 4/1993 | Japan . |
| 6-100594 | 4/1994 | Japan . |
| 59-501714 | 10/1994 | Japan . |
| 7-75577 | 3/1995 | Japan . |
| 93/09247 | 5/1993 | WIPO . |

OTHER PUBLICATIONS

Morrison, Ann Rev. Immunol. 10:239–65, 1992.
Wiley et al., "The Structure and Function of the Hemagglutinin Membrane Glycoprotein of Influenza Virus", Ann. Rev. Biochem. 1987, 56: pp. 365–394.

Green et al., "Immunogenic Structure of the Influenza Virus Hemagglutinin", Cell, vol. 28, pp. 477–487, Mar. 1982.

Shaw et al., "Characterization for A Mouse/Human Chimeric Monoclonal Antibody (17–1A) to A Colon Cancer Tumor–Associated Antigen[1]", The Journal of Immunology, vol., 138, pp. 4534–4538, No. 12 Jun. 15, 1987.

Morrison et al., "Chimeric Human Antibody Molecules: Mouse Antigen–Binding Domains with Human Constant Region Domains", Proc. Natl. Acad. Sci USA, vol. 81, pp. 6851–6855, Nov. 1984.

Inventor's speech (abstract) made at the 1st China–Japan International Congress of Virology. May 26–28, 1992. Copies of Tables 1–2, FIGS. 1–3 used in the speech are also enclosed.

Okuno et al., "A Common Neutralizing Epitope Conserved between the Hemagglutinins of Influenza A Virus H1 and H2 Strains", Journal of Virology, May 1993, pp. 2552–2558.

S. Clarke et al., "The Balb/c Secondary Response to the Sb Site of Influenza Virus Hemagglutinin", The Journal of Immunology, vol. 145, No. 7, pp. 2286–2296, Oct. 1, 1990.

*Primary Examiner*—Lila Feisee
*Assistant Examiner*—Nancy A. Johnson
*Attorney, Agent, or Firm*—Wenderoth, Lind & Ponack

[57] ABSTRACT

An isolated DNA is provided coding for the variable region of an anti-human influenza A type virus antibody having the following characteristics: (a) specifically binds to the stem region of haemaggulutinin molecule of H1N1 and H2N2 subtypes of human influenza A type virus but does not specifically bind to the stem region of haemaggulutinin molecule of H3N2 subtype; and (b) has a neutralization activity for the H1N1 and H2N2 subtypes of human influenza A type virus but no neutralization activity for the H3N2 subtype.

5 Claims, 2 Drawing Sheets

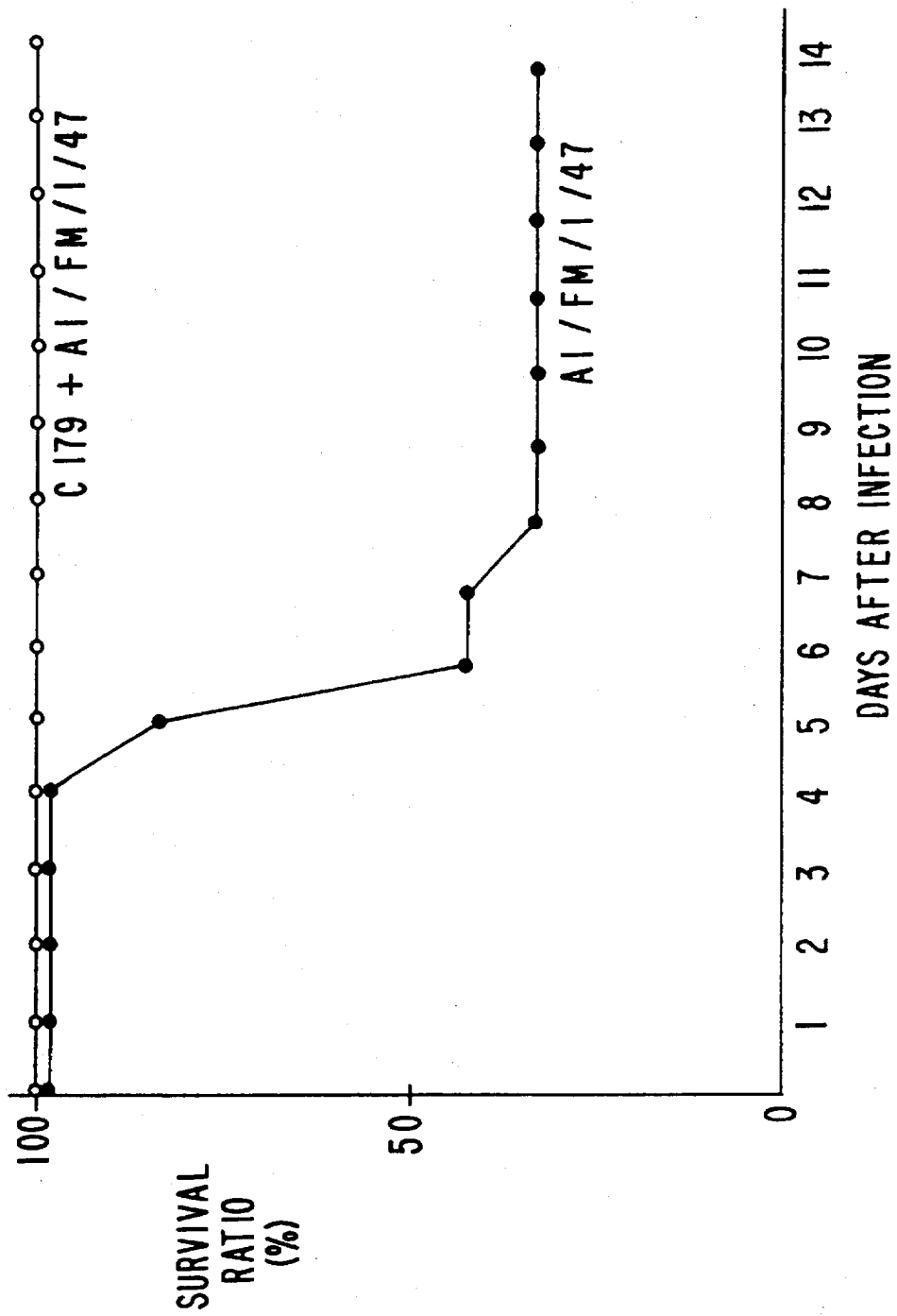

DNA CODING FOR VARIABLE REGION TO HUMAN INFLUENZA A TYPE VIRUS

[FIELD OF INDUSTRIAL APPLICATION]

This invention relates to a DNA which codes for the variable region of a mouse monoclonal antibody against influenza A type virus. It is useful in the production of artificial antibodies through genetic engineering techniques.

[PRIOR ART]

There are three types (A, B and C) of influenza viruses and the worldwide prevalence of influenza costing a large number of deaths is caused by human influenza A type virus.

Influenza A type virus is further classified into various subtypes depending on the antigenicities of haemagglutinin (hereinafter referred to simply as HA) and neuraminidase (hereinafter referred to simply as NA) which are viral surface proteins. There have been known so far three subtypes of human influenza A type viruses, namely, the H1N1, H2N2 and H3N2 subtypes.

The HA of influenza A type virus comprises two structurally distinct regions, namely, a globular head region and a stem region. The globular head region contains a receptor binding site which is responsible for virus attachment to a target cell and participates in the haemagglutination activity of HA. On the other hand, the stem region contains a fusion peptide which is necessary for membrane fusion between the viral envelope and an endosomal membrane of the cell and thus relates to fusion activity [Wiley et al., *Ann. Rev. Biochem.*, 56, 365–394 (1987)].

All of anti-HA antibodies, which have been obtained hitherto as an antibody capable of recognizing the H1N1 and H2N2 subtypes, recognize the globular head region of HA. However, this region most frequently undergoes antigen mutation. Therefore, these antibodies are not common to the subtypes of human influenza A type virus and, further, lose the recognizing ability with antigenic changes in the HA of the virus.

On the other hand, Green et al. have synthesized a polypeptide based on an amino acid sequence in the stem region of HA of the H3N2 subtype and obtained antibodies against this polypeptide. However, these antibodies have a low neutralization activity (Published Japanese Translation of PCT Patent Applications from Other Countries, No. 501714/1984). Furthermore, the polypeptide per se employed as an antigen does not react with rabbit antiviral serum obtained by immunizing with the H3N2 subtype, which suggests that there is a problem from the viewpoint of antigenicity too [*Cell*, 28, 477–487 (1982)]

Human influenza A type virus periodically changes types of HA and NA and thus causes wide prevalence. It is often observed that vaccinization before winter, i.e, the season of prevalence, produces no effect, since the prevalence is caused by a virus of a different type. However, if an antigen site which is common to virus subtypes in HA and NA molecules and hardly undergoes antigen mutation, especially an antibody which recognizes the stereostructure and has a neutralization activity can be acquired, this antibody is usable in the diagnosis, prevention and treatment of infection with influenza A type virus.

This present inventors obtained the anti-human influenza A type virus antibody which is capable of cross-recognizing the subtypes of influenza A type virus and has a virus neutralization activity and has the characteristics (a) and (b); (a) recognizing the stem region of haemaggulutinin molecule of the H1N1 and H2N2 subtypes of human influenza A type virus but not recognizing the stem region of haemaggulutinin molecule of the H3N2 subtype thereof; and (b) having a neutralization activity for the H1N1 and H2N2 subtypes of human influenza A type virus but no neutralization activity for the H3N2 subtype thereof.

One example of this anti-human influenza A type virus antibody is a monoclonal antibody C179 (hereinafter referred to simply as C179) obtained from Hybridoma C179 (FERM BP-4517). Also the preventive effect of C179 on influenza A type virus has been confirmed (Japanese Patent Application No. 272538/1992).

[PROBLEMS TO BE SOLVED BY THE INVENTION]

However this monoclonal antibody which is capable of cross-recognizing the subtypes of influenza A type virus and has a virus neutralization activity has been derived from mouse hybridomas. Therefore the immunogenicity of this mouse antibody imposes various restrictions on the application thereof to clinical medicine as a drug for human being. That is to say, the use of a mouse antibody frequently induces an immune response and causes an anaphylactic shock. Further, repeated administration of the mouse antibody lowers the potency of the effect of the antibody or extremely quickens its clearance from the blood. Therefore such a mouse antibody substantially ranks low in the therapeutics. Although these difficulties encountering in the use of a mouse antibody can be overcome by using a human monoclonal antibody clinically, it is highly difficult to steadily produce a human monoclonal antibody corresponding to, for example, C179 while sustaining the desired specificity and affinity thereof.

It is also known that a cell line producing a monoclonal antibody would generally suffer from a decrease in the antibody productivity with repetitive subculturing. In order to solve this problem, it is needed to examine the possibility of mass expression through gene transduction following the cell cloning of antibody-producing cells or the cloning of an antibody gene.

From these viewpoints, it is considered that when a chimeric antibody wherein the variable region of an antibody derived from a species is bound to the constant region of another antibody derived from a different species (in usual, a chimeric antibody is composed of the variable region of a mouse antibody bound to the constant region of a human antibody) is constructed through recombinant DNA techniques, then an antibody substantially having a low immunogenicity and being suitable for clinical uses compared with the mouse antibody can be obtained, since the major part of this chimeric antibody originates in human being. Chimeric antibodies have been reported by Shaw et al., *J. Immun.*, 138, 4534 (1987), Morrison, S., et al., *Pro. Nat. Acad. Sci. USA*, 81, 6851–6855 (1984), etc. and regarded as a general idea. In recent years, therefore, attempts have been made to develop, for example, a chimeric antibody composed of a variable region originating in mouse and a human constant region, a bispecific chimeric antibody having two antigen specificities different from each other, single-stranded antibody and an oligopeptide corresponding to the complementarity-determining region (CDR) having an antibody activity. In the production of these antibodies through genetic engineering techniques and the development of improved antibodies, it is essentially required to isolate a certain gene and to clarify its structure including the amino acid sequence thereof. It has been well known in the art that the specificity of an antibody is restricted to a particular region, i.e., CDR in the variable region thereof. Thus there have been widely effected amino acid replacements in CDR in order to, for example, improve the affinity of an antibody. Accordingly, it is particularly important to clarify the DNA sequence and amino acid sequence of CDR.

It is an object of the present invention to provide a DNA coding for the variable region of a mouse monoclonal antibody which is useful in the production of a chimeric antibody being hardly recognized as a foreign substance in a human body or an artificial antibody having the complementarity-determining region transplanted into a human antibody exclusively, and a DNA coding for the complementarity-determining region of the above-mentioned variable region.

[MEANS FOR SOLVING THE PROBLEMS]

To sum up, the first invention relates to a DNA coding for the variable region of the anti-human influenza A type virus antibody having the following characteristics (a) and (b);
(a) recognizing the stem region of haemaggulutinin molecule of the H1N1 and H2N2 subtypes of human influenza A type virus but not recognizing the stem region of haemaggulutinin molecule of the H3N2 subtype thereof; and (b) having a neutralization activity for the H1N1 and H2N2 subtypes of human influenza A type virus but no neutralization activity for the H3N2 subtype thereof.

The second invention relates to a DNA coding for CDR in a DNA which codes for the variable region of the anti-human influenza A type virus antibody of the first invention.

The term "variable region" as used herein means an amino acid sequence which contains at least the CDR in its amino acid sequence.

In order to clone the DNA coding for the variable region of the anti-human influenza A type virus antibody and having the characteristics (a) and (b) as described above, it is necessary to prepare hybridomas capable of producing the above-mentioned antibody as a gene source. As such hybridomas, Japanese Patent Application No. 272538/1992 has disclosed mouse hybridomas producing C179 (Hybridoma C179: FERM BP-4517) and the properties of this antibody. A method for the preparation of these hybridomas and the properties of C179 will be described in Referential Example A hereinafter.

To clone the target DNA which codes for the variable region of the mouse monoclonal antibody, the hybridomas are disrupted to thereby prepare the full RNA. By using the full RNA, a single-stranded cDNA is prepared in accordance with the Gubler-Hoffman method.

Next, the significant part of the above-mentioned cDNA is specifically amplified by the DNA extension method with the use of oligonucleotide primers. For the amplification of the heavy chain variable region of the mouse monoclonal antibody, oligonucleotide primers represented by the SEQ ID NO: 11 and 12 in the sequence listing are used respectively as a 5'-terminal primer and a 3'-terminal primer for PCR.

The oligonucleotide primer represented by the SEQ ID NO: 11 in the sequence listing is hybridized with the heavy chain leader sequence, while the oligonucleotide primer represented by the SEQ ID NO: 12 in the sequence listing is hybridized with the heavy chain constant region. For the amplification with the use of the light chain variable region primer of the mouse monoclonal antibody, the oligonucleotide primer represented by the SEQ ID NO: 13 in the sequence listing is used as a 3'-terminal primer. This primer is hybridized with the light chain constant region of the mouse monoclonal antibody.

On the other hand, C179 is highly purified and the N-terminal amino acid sequences of its heavy chain and light chain are determined. The N-terminal amino acid sequence of the heavy chain of the monoclonal antibody and the N-terminal amino acid sequence of the light chain thereof are represented by the SEQ ID NO: 14 and 15 in the sequence listing respectively.

The product of the above-mentioned amplification is integrated into an appropriate vector such as pT7 blue T vector (manufactured by Novagen) or pGEM-4ZDNA (manufactured by Promega) to thereby give a plasmid containing a DNA fragment which codes for the target variable region of the monoclonal antibody.

The sequence of the cloned DNA is determined and the sequences represented by the SEQ ID NO: 3 and 4 in the sequence listing are compared with the DNA sequences anticipated from those represented by the SEQ ID NO: 14 and 15 in the sequence listing. As a result, a DNA which is an example of the first invention of the present invention and amino acid sequences coded for by this DNA are provided. These sequences are represented by the SEQ ID NO: 1 and 2 in the sequence listing. Cloning of the target DNA and the determination of its sequence will be described in greater detail in Examples 1 and 2 hereinafter.

The present invention further provides a DNA which codes for the CDR of each variable region.

The variable region composed of the heavy chain and the light chain forms an antigen binding domain. This region located over the heavy and light chains contains 4 framework regions which have been relatively well conserved. These regions are ligated with 3 CDRs. These CDRs are determined through a comparison with known amino acid sequences in the variable region. The amino acid sequences of the CDRs provided by the present invention are described in the SEQ ID NO: 5 to 10 in the sequence listing.

The present invention provides a variable region and a CDR which are useful as a material for producing chimeric antibodies or humanized antibodies and DNAs coding for the same.

By using the DNAs of the present invention coding for the heavy chain variable region and the light chain variable region, Fab, Fv, scFv, etc. can be produced through genetic engineering techniques. scFv is a single-stranded polypeptide constructed by binding the heavy chain variable region to the light chain variable region via a spacer consisting of several amino acid residues.

An example of the plasmid to be used in the construction of Fv is a plasmid pM13Fv described in Japanese Patent Application No. 246184/1993. An *Escherichia coli* JM109 strain having this plasmid introduced thereinto was named *Escherichia coli* JM1O9/pM13Fv. This strain was deposited on Jun. 22, 1993 at National Institute of Bioscience and Human-Technology Agency of Industrial Science and Technology in accordance with tha Budapest Treaty under the accession number FERM BP-4968.

FIG. 1 is a schematic illustration of the gene sequence of the plasmid pM13Fv.

In FIG. 1, the X gene corresponds to the part located between Hind III and SalI, the Y gene corresponds to the part located between SalI and SalI and the Z gene corresponds to the part located between SalI and EcoRI. The gene sequence located between HindIII and EcoRI sites, which corresponds to X-Y-Z, is described in the SEQ ID NO: 16 in the sequence listing.

In the plasmid pM13Fv, the X-Y-Z genes has been inserted between the HindIII and EcoRI sites of a plasmid pTZ19R (manufactured by Pharmacia) which is a common phagemid vector. The X gene existing in the downstream of the promoter originating in the vector comprises an SD sequence (Shine-Dalgarno sequence) followed by the first open reading frame by which a secretory signal peptide and the heavy chain variable region (hereinafter referred to simply as $V_H$) are coded for.

In the downstream thereof, it has another SD sequence followed by the second open reading frame by which a secretory signal peptide and the light chain variable region (hereinafter referred to simply as $V_L$) are coded for. A restriction enzyme SalI site (base no. 891 to 896 in the SEQ ID NO: 16) is located at the 3'-terminal part of the $V_L$ gene. Following the open reading frame of the $V_L$ gene, the Y gene containing a gene (SEQ ID NO: 17) which codes for a partial sequence (ΔcpIII polypeptide) of a linear phage coat protein III exists.

That is to say, the second open reading frame codes for a fused polypeptide comprising the secretory signal polypeptide, $V_L$ and the ΔcpIII polypeptide. The Y gene is ligated to the Z gene at the restriction enzyme SalI site which is located in the further downstream of the ΔcpIII polypeptide gene coded for by the Y gene. The Z gene is a gene containing a gene (SEQ ID NO: 18) which codes for a polypeptide containing two Fc binding domain-like structures of protein A.

When this pM13Fv having the above-mentioned structure is completely digested with the restriction enzyme SalI, the Y gene is excised therefrom. After eliminating the Y gene, the plasmid is subjected to self ligation. Thus the X gene is ligated to the Z gene at the SalI site to thereby give a plasmid pFV-PP.

Then the polypeptide containing two Fc binding domain-like structures of protein A, which is coded for by the Z gene, is ligated in such a manner as to follow the second open reading frame of the X gene. After eliminating the Y gene by digesting the plasmid pM13Fv with the restriction enzyme SalI, namely, the second open reading frame coded for by the residual gene codes for a fused polypeptide composed of the secretory signal peptide, $V_L$ and the polypeptide containing two Fc binding domain-like structures of protein A.

Into the part corresponding to the X gene in this plasmid pFv-PP, an Fv gene originating in a monoclonal antibody against hen egg lysozyme (hereinafter referred to simply as HEL) has been inserted. In practice, there exist restriction enzyme sites in order to facilitate the replacement of the Fv gene. That is to say, the plasmid pFv-PP is cleaved at the PstI site located in the base no. 115 to 120 in the DNA sequence represented by the SEQ ID NO: 36 and at the SmaI site located in the base no. 467 to 472 therein to thereby eliminate the $V_H$ gene having been inserted thereinto. Then an arbitrary $V_H$ gene which has been prepared in such a manner as to suit the open reading frame may be inserted thereinto. Such a PstI-SmaI fragment suiting the open reading frame may be a DNA synthesized by using a DNA synthesizer. Alternatively, a DNA fragment obtained by digesting a DNA fragment, which has been prepared by the PCR method with the use of a primer for a $V_H$ gene amplification synthesized by a conventional method in such a manner as to contain the PstI site or the SmaI site, with PstI or SmaI may be used therefor. Similarly, the $V_L$ gene can be replaced by a DNA fragment coding for a $V_L$ gene between the SacI site located in the base no. 583 to 588 in the DNA sequence represented by the SEQ ID NO: 36 in the sequence listing and the SalI site located in the base no. 891 to 896 therein.

The plasmid pFv-PP has been converted into a form capable of expressing a fused polypeptide of a polypeptide containing an antibody variable domain with another polypeptide having two Fc binding domain-like structures of protein A.

This fused polypeptide of a polypeptide containing the antibody variable domain with another polypeptide having an Fc affinity is a highly useful one. The first reason therefor resides in that it can be easily purified. For example, the fused polypeptide can be recovered from the culture by using a resin onto which a polypeptide or a protein containing Fc has been immobilized. The second reason therefor resides in that a stable multivalent antigen complex can be formed by mixing this fused polypeptide with a polypeptide or a protein containing Fc, for example, human IgG. Because of being multivalent, this complex has a higher binding stability than that of a monovalent one and is useful in, for example, ELISA, Western blotting, etc. Also, the fused polypeptide is useful from the viewpoint that it can be easily detected depending on the properties of the Fc-containing polypeptide to be mixed therewith. Effective examples of the polypeptide containing the antibody variable site to be used for the formation of such a fused polypeptide include an Fv fragment, an scFv fragment and an Fab fragment.

For example, the DNA represented by the SEQ ID NO: 3 is amplified by the PCR method with the use of a primer represented by the SEQ ID NO: 19 for the PstI site introduction and another primer represented by the SEQ ID NO: 20 for the SmaI site introduction. Thus a DNA coding for $V_H$ to be inserted into the plasmid pFvPP (hereinafter referred to simply as the $V_H$ insert) is prepared. On the other hand, the DNA represented by the SEQ ID NO: 4 is amplified by the PCR method with the use of a primer represented by the SEQ ID NO: 21 for the SacI site introduction and another primer represented by the SEQ ID NO: 22 for the SalI site introduction. Thus a DNA coding for $V_L$ to be inserted into the plasmid pFv-PP (hereinafter referred to simply as the $V_L$ insert) is prepared. Next, the plasmid pFv-PP is cleaved with PstI and SmaI and the $V_H$ insert is inserted into the plasmid part.

Subsequently, the plasmid having the $V_H$ insert is cleaved with SacI and SalI and the $V_L$ insert is inserted into the plasmid part. Thus the plasmid having the DNA coding for $V_H$ and $V_L$ of the present invention inserted thereinto can be constructed. This plasmid is named T19C179FvproA while an *Escherichia coli* BMH71-18 strain transformed by this plasmid is named *Escherichia coli* BMH71-18/T19C179FvproA. By incubating this *E. coli* strain, the $V_H$ and $V_L$ of the present invention can be expressed as a fused polypeptide of Fv with a polypeptide having two Fc binding domain-like structures of protein A. This fused polypeptide can be easily purified by using an Fc-binding carrier, for example, IgG-Sepharose 6FF (manufactured by Pharmacia) and is usable as an artificial antibody for detecting influenza A type virus.

Also, the $V_H$ and $V_L$ of the present invention can be expressed in the form of scFv.

For example, the DNA represented by the SEQ ID NO: 3 is amplified by the PCR method with the use of the above-mentioned primer represented by the SEQ ID NO: 19 and another primer represented by the SEQ ID NO: 23 for introducing a linker. Next, the oligonucleotides represented by the SEQ ID NO: 24 and 25 are annealed and then cleaved with PstI and SacI to thereby give a linker for the preparation of scFv. The above-mentioned plasmid T19C179FvproA is cleaved with PstI and SacI and the linker is inserted into the plasmid part. Then this plasmid is cleaved with BamHI and PstI and the above-mentioned PCR-amplified DNA is inserted thereinto. Thus a plasmid having a DNA, wherein the DNA coding for $V_H$ is ligated to the DNA coding for $V_L$ with a linker, inserted thereinto can be constructed. This plasmid is named T19C179ScFVproA while an *Escherichia coli* BMH71-18 strain transformed by this plasmid is named *Escherichia coli* BMH71-18/T19C179ScFVproA This strain was deposited on Feb. 28, 1994 at National Institute of Bioscience and Human-Technology Agency of Industrial Science and Technology (1-3, Higashi 1 chome Tsukuba-shi Ibaraki-ken 305,Japan) in accordance with the Budapest Treaty under the accession number FERM BP-4969.

By incubating this *E. coli* strain, the $V_H$ and $V_L$ of the present invention can be expressed as a fused polypeptide of scFv with a polypeptide having an two Fc binding domain-like structures of protein A. This fused polypeptide can be also easily purified by using IgG-Sepharose 6FF and is usable as an artificial antibody for detecting influenza A type virus. Further, a stop codon can be prepared in the next position of the DNA coding for $V_L$ of each of the plasmids T19C179FvproA and T19C179ScFVproA by the site-specific mutation method. The modified plasmid thus formed is usable as a plasmid for the Fv expression or the scFV expression with the use of the DNA coding for $V_H$ and $V_L$ of the present invention.

As discussed above in detail, the present invention provides a gene coding for $V_H$ of a gene coding for anti-human influenza A type virus antibody, a gene coding for $V_L$ of the same and a gene coding for CDR of the same. These genes are useful in the preparation of Fv, scFv, Fab, artificial antibodies containing the same, chimeric antibodies, humanized antibodies and single CDR polypeptides and the proteins and polypeptides thus obtained are useful in the diagnosis and treatment of human influenza A type virus.

By effecting hybridization under strict conditions with the use of the genes of the present invention thus obtained as a probe, genes coding for proteins and polypeptides, which are similar in properties to the $V_H$, $V_L$ and CDR of the present invention, can be obtained, though the obtained genes are somewhat different in sequence from the genes of the present invention. The term "strict conditions" as used herein has the following meaning. Namely, a nylon membrane having a DNA immobilized thereon is hybridized with a probe at 65° C. for 20 hours in a solution containing 6×SSC (1×SSC corresponding to 8.76 g of sodium chloride and 4.41 g of sodium citrate dissolved in 1 l of water), 1% of sodium lauryl sulfate, 100 µg/ml of salmon sperm DNA and 5× Danhardt's (containing 0.1% portions of bovine serum albumin, polyvinylpyrrolidone and Ficoll).

The $V_H$, $V_L$ and CDR of the present invention may be those having deletion, substitution, insertion, inversion, addition or rearrangement of amino acids, so long as the activities thereof are not affected thereby. Also, genes coding for these proteins and polypeptides may be prepared through genetic engineering techniques and used.

An antibody prepared by using the genes of the present invention recognizes the H1N1 and H2N2 subtypes in common but not the H3N2 subtype. Therefore human influenza A type virus in a specimen can be readily typed at a high sensitivity by using the antibody prepared with the use of the genes of the present invention in a combination with an antibody capable of recognizing the H3N2 subtype [for example, a monoclonal antibody AI3C (developed by Takara Shuzo Co., Ltd.; development name: F49) produced by a hybridoma AI3C described in Japanese Patent Application No. 115216/1993] and a polyclonal antibody (manufactured by Takara Shuzo Co., Ltd.) for detecting human influenza B type virus. A hybridoma AI3C was deposited on Nov. 11, 1992 at National Institute of Bioscience and Human-Technology Agency of Industrial Science and Technology (1-3, Higashi 1 chome Tsukuba-shi Ibaraki-ken 305, Japan) in accordance with the Budapest Treaty under the accession number FERM BP-4516. Furthermore, the antibody prepared by using the genes of the present invention recognizes the H1N1 and H2N2 subtypes in common and has a neutralization activity. Thus it is useful in the prevention and treatment of diseases in which viruses of these subtypes participate.

To illustrate the anti-influenza A type virus antibodies and Fv and scFv expression plasmids employed in the present invention, the following Referential examples will be given.

REFERENTIAL EXAMPLE A

1. Preparation of viruses:

Virus strains of the H1N1 subtype used included A/Bangkok/10/83, A/Yamagata/120/86, A/Osaka/930/88, A/Suita/1/8 (each being a stock of the Research Institute for Microbial Diseases, Osaka University),A/PR/8/34(ATCC VR-95)and A1/FM/1/47 (ATCC VR-97)were used. Virus strains of the H2N2 subtype used included A/Okuda/57, A/Adachi/2/57, A/Kumamoto/1/65, A/Kaizuka/2/65 and A/Izumi/5/65(each being a stock of the Research Institute for Microbial Diseases, Osaka University) were used. Virus strains of the H3N2 subtype, used included A/Fukuoka/C29/85, A/Sichuan/2/87, A/Ibaraki/1/90, A/Suita/1/90, A/Kitakyushu/159/93(each being a stock of the Research Institute for Microbial Diseases, Osaka University) and A2/Aichi/2/68(ATCC VR-547) were used. A strain of influenza B type virus used was B/Nagasaki/1/87. Each strain was inoculated into the allantoic cavity of an embryonated hen egg aged 11 days, incubated at 34° C. for 4 days and then harvested.

2. Preparation of monoclonal antibodies:

(1) Balb/c mice were immunized with two doses of A/Okuda/57 strain (320 HAU) prepared in the above Referential example A-1, which had been suspended in Freund's complete adjuvant before use, via intraperitoneal injection one month apart. One month thereafter, the mice were boosted by intraperitoneally injecting a suspension of the same antigen (320 HAU) in PBS. Three days thereafter, the spleen of each animal was taken out and thus spleen cells were prepared.

Mouse myeloma cells were prepared by incubating. p3x63Ag8 cells in a DME medium containing 10% of fetal bovine serum for 2 days after passage and then washing with physiological saline before cell fusion. The spleen cells were mixed with the myeloma cells at a ratio by cell count of 1:5. After centrifuging and removing the supernatant, the precipitated cell clusters were thoroughly loosened and then added to 1 ml of a mixture [polyethylene glycol 4000 (2 g), MEM (2 ml), and dimethyl sulfoxide] under stirring. After maintaining at 37° C. for 5 minutes, MEM was slowly added thereto so as to adjust the total amount to 10 ml. After the mixture was centrifuged, the supernatant was removed and the cell clusters were gently loosened. 30 ml of a normal medium (PRMI-1640 containing 10% of fetal bovine serum) was added thereto and the cells were slowly suspended with the use of a measuring pipet.

The suspension was pipetted into a 96-well incubation plate and incubated in an incubator containing 5% of $CO_2$ at 37° C. for 24 hours. Then HAT medium was added thereto and the incubation was continued for 10 to 14 days. Subsequently, a part of the culture supernatant was sampled and subjected to hybridoma screening.

(2) To obtain a monoclonal antibody undergoing a cross reaction between influenza A type virus subtypes, the above-mentioned culture supernatant, which had not been diluted, was used as a primary antibody and a staining test on MDCK cells infected with the three subtypes (H1N1, H2N2 and H3N2) was effected. The staining test was carried out in accordance with the above-mentioned method described in Journal of Clinical Microbiology. Specifically, the MDCK cells infected with the human influenza A type virus subtype strains (H1N1: A/Yamagata/120/86, H2N2: A/Okuda/57, H3N2: A/Fukuoka/C29/85) were rinsed with PBS (pH 7.4) on 96-well microtiter plates (Falcon 3072; manufactured by Becton Dickinson Labware) and fixed with absolute ethanol at room temperature for 10 minutes. Then these cells were continuously treated with 4 antibodies [the above-mentioned culture supernatant containing the monoclonal antibody, rabbit anti-mouse immunoglobulin G serum (manufactured by Organon Teknika) diluted 1000-fold, goat anti-rabbit immunoglobulin G serum (manufactured by Organon Teknika) diluted 500-fold, and peroxidase-rabbit anti-peroxidase complex (manufactured by Organon Teknika) diluted 1000-fold, each for 40 minutes, and the cells thus treated were washed with PBS. Finally, the peroxidase reaction was effected by the method of Graham and Karnovsky [see *J. Histochem. Cytochem.*, 14, 291–302 (1966)] with the use of 0.01% $H_2O_2$ and 0.3 mg/ml of 3,3'-diaminobenzidine tetrahydrochloride in PBS. The stained cells were observed under an ordinary light microscope to sort antibodies recognizing respectively the H1N1 subtype-infected MDCK cells and the H2N2 subtype-infected MDCK cells. Next, the cells in the wells where the production of these antibodies had been confirmed were taken out and treated by the limiting dilution thrice to thereby clone the target cells. The hybridoma strain thus cloned was named Hybridoma C179, while the monoclonal antibody produced thereby was named monoclonal antibody C179.

The Hybridoma C179 was deposited on Jan. 28, 1993 at National Institute of Bioscience and Human-Technology Agency of Industrial Science and Technology (1-3 Higashi 1 chome Tsukuba-shi Ibaraki-ken 305,Japan) in accordance with the Budapest Treaty under the accesion number FERM BP-4517.

(3) $5 \times 10^6$/animal of the above-mentioned hybridomas were intraperitoneally administered to Balb/c mice treated with pristane. Ten to 21 days thereafter, the ascites of a mouse having ascites cancer thus induced was sampled and centrifuged at 3000 rpm for 5 minutes to thereby remove solid components and give an ascites fluid. This fluid contained about 5 mg/ml of the monoclonal antibody C179 (hereinafter referred to simply as C179). After purifying with Protein A-Sepharose 4B (manufactured by Pharmacia), C179 was confirmed as an antibody of the IgG2a type.

3. Properties of monoclonal antibody:

(1) A 100-fold dilution of the ascites fluid as described in the above Referential example A-2-(3) was diluted stepwise and the staining test as described in the above Referential example A-2-(2) was effected to examine the antigen recognizing characteristics of C179. The H1N1 subtype strains used included A/PR/8/34, A/Bangkok/10/83, A/Yamagata/120/86, A/Osaka/930/88, A/Suita/1/89 and A1/FM/1/47. The H2N2 subtype strains used included A/Okuda/57, A/Adachi/2/57, A/Kumamoto/1/65, A/Kaizuka/2/65 and A/Izumi/5/65. The H3N2 subtype strains used included A/Aichi/2/68, A/Fukuoka/C29/85, A/Sichuan/2/87, A/Ibaraki/1/90, A/Suita/1/90 and A/Kitakyushu/159/93. Further, B/Nagasaki/i/87 was used as an influenza B type virus strain.

C179 recognized all of the H1N1 subtype and H2N2 subtype strains but did not recognize the H3N2 subtype strains and the influenza B type virus strain.

(2) The neutralization activity of the antibody was determined by effecting the above-mentioned influenza virus rapid focus reduction neutralization test in accordance with the description of *Arch. Virol.*, 86, 129–135 (1985) and *Microbiol. Immunol.*, 29, 327–335 (1985). The ascites fluid of the above Referential example A-2-(3) was used as an antibody, to which was added thrice by volume as much a receptor destroying enzyme (RDE: manufactured by Takeda Chemical Industries, Ltd.) solution before the use. After reacting at 37° C. for 18 hours, the RDE was inactivated by heating at 56° C. for 45 minutes. Finally, a 16-fold dilution of the ascites fluid was prepared and subjected as a test sample to the determination as will be described hereinbelow.

Namely, $10^4$/well of MDCK cells were pipetted into 96-well microplates. On the next day, the above-mentioned antibody (16-fold dilution) diluted in 4 steps was mixed with the equal amount of the suspension of each virus strain of 30 focus-forming units/well prepared in the above Referential example A-3-(1), and the mixture was kept at 37° C. for 1 hour. Then 25 µl of this mixture was pipetted into the wells of the microtiter plates containing the above-mentioned MDCK cells and kept at 37° C. for 30 minutes. Then the solution in each well was removed and the well was rinsed with PBS. Next, MEM containing 0.5% of tragacanth gum (manufactured by Wako Pure Chemical Industries, Ltd.) and 5 µg/ml of trypsin was added thereto. After being kept at 37° C. for 20 to 24 hours, the solution added above was removed and each well was rinsed with PBS. Then the cells were fixed by treating with absolute ethanol at room temperature for 10 minutes. Then these cells were dried and stained in accordance with the staining test as described in the above Example 2-(2). After the completion of the staining, the cells were rinsed with tap water and dried. Then the stained focus were counted under a light microscope.

C179 inhibited the focus formation of all of the H1N1 subtype and H2N2 subtype strains and had a potent virus neutralization activity. On the other hand, it exerted no effect on the focus formation by the H3N2 subtype strains and the influenza B type virus strain. The plaque reduction neutralization test gave similar results.

(3) The haemagglutination inhibition (HI) activity of the antibody was examined by the following method. The antibody (32-fold dilution) which had been treated with RDE in the same manner as the one described in the above Referential example A-3-(2) was diluted stepwise and mixed with each virus strains (16 HAU) as described in the above Referential example A-3-(1) to effect a reaction at room temperature for 30 minutes. After adding avian erythrocytes and well mixing, the effect of the antibody on the haemagglutination activity of each virus strain was examined. It was found that the haemagglutination activity of none of the virus strains was affected by C179.

(4) The fusion inhibition activity of the antibody was determined by the above method as described in *Nature*, 300, 658–659 (1982) with a few slight modifications. Namely, monolayer cultures of CV-1 cells were infected with each of the virus strains as described in the above Referential example A-3-(1). 24 hours after the inoculation, the cells were washed twice with DMEM and then kept at 37° C. in DMEM containing 10 μg/ml of trypsin for 15 minutes. Subsequently, the cells were washed twice with DMEM and kept at 37° C. in the ascites fluid of the above Referential example 2-(3) diluted with DMEM for 30 minutes. Thereafter, the cells were treated for 2 minutes at 37° C. with a fusion medium (RPMI free from $Na_2CO_3$, containing 0.2% bovine serum albumin, 10 mM MES and 10 mM HEPES) adjusted to pH 5.0. Then the cells were washed twice with DMEM to remove the fusion medium, and then kept at 37° C. for 3 hours in DMEM containing 2% of fetal bovine serum. Next, the cells were fixed with absolute methanol and subjected to Giemsa's staining. Then the formation of polykaryons was examined under a light microscope.

C179 inhibited the polykaryon formation by all of the H1N1 and H2N2 subtype strains but did not inhibit the formation by the H3N2 subtype strain and the influenza B type virus strain.

As discussed above, C179 is an antibody which specifically recognizes the H1N1 and H2N2 subtypes, inhibits membrane fusion of viruses and exhibits a neutralization activity. Table 1 summarizes these results.

TABLE 1

| | Antibody titers of C179 measured by | | | |
|---|---|---|---|---|
| Virus | Staining activity | Neutralization activity | HI activity | Fusion inhibition activity |
| H1N1 | | | | |
| A/PR/8/34 | 1,638,400 | 512 | <32 | + |
| A/Bangkok/10/83 | 1,638,400 | 512 | <32 | + |
| A/Yamagata/120/86 | 409,600 | 1,024 | <32 | + |
| A/Osaka/930/88 | 409,600 | 512 | <32 | + |
| A/Suita/1/89 | 409,600 | 1,024 | <32 | + |
| A1/FM/1/47 | 409,600 | 512 | <32 | + |
| H2N2 | | | | |
| A/Okuda/57 | 1,638,400 | 1,024 | <32 | + |
| A/Adachi/2/57 | 1,638,400 | 1,024 | <32 | + |
| A/Kumamoto/1/65 | 409,600 | 1,024 | <32 | + |
| A/kaizuka/2/65 | 409,600 | 2,048 | <32 | + |
| A/Izumi/5/65 | 409,600 | 1,024 | <32 | + |
| H3N2 | | | | |
| A2/Aichi/2/68 | <100 | <16 | <32 | – |
| A/Fukuoka/C29/85 | <100 | <16 | <32 | – |
| A/Sichuan/2/87 | <100 | <16 | <32 | – |
| A/Ibaraki/1/90 | <100 | <16 | <32 | – |
| A/Suita/1/90 | <100 | <16 | <32 | – |
| A/Kitakyusha/159/93 | <100 | <16 | <32 | – |
| B | | | | |
| B/Nagasaki/1/87 | <100 | <16 | <32 | – |

In the above Table 1, each number represents the dilution ratio of the ascites fluid of the Referential example A-2-(3), a staining titer is expressed in the maximum dilution ratio of the ascites fluid whereby cells can be stained in the staining test, while a neutralization activity is expressed in the maximum dilution ratio of the ascites fluid whereby the formation of focus can be suppressed up to a level corresponding to one half of the focus count in the control lot wherein no antibody is added. Symbol + means that polykaryon formation is completely inhibited by a 1000-fold dilution of the ascites fluid, while symbol – means that polykaryon formation is not inhibited even by using a 10-fold dilution of the ascites fluid. A 32-fold dilution of the ascites fluid shows no HI activity.

4. Preventive effect on influenza A type virus:

In order to examine the preventive effect of C179, an influenza A type virus infection test was carried out by using mice. 1 ml/animal of a C179 solution (1 mg/ml in PBS) was intraperitoneally administered to 10 Balb/c mice. After 1 day, 25 μl of a 1000-fold dilution of A1/FM/1/47 (4000 HAU) of the H1N1 subtype was intranasally administered. As a control, 12 mice were inoculated with the virus alone.

As FIG. 2 shows, 8 mice in the control group died (two mice after 5 days, five after 6 days and one after 8 days). Other surviving mice in this group were extremely weakened. In contrast, the mice administered with C179 showed no abnormality and all remained healthy even after 14 days.

FIG. 2 is a graph showing the survival ratios of the C179-administered group and the control group wherein the ordinate indicates the survival ratio while the abscissa indicates the time (days) after the infection with the virus.

REFERENTIAL EXAMPLE B

Construction of Plasmids pFv-PP and pM13Fv:

A plasmid pSW1$V_H$D1.3$V_K$D1.3 coding for an Fv fragment originating in a monoclonal antibody D1.3 against HEL was provided by Dr. Gregg Winter (Cambridge, UK), though it somewhat differed in the sequence from the one reported in references. In this plasmid pSW1$V_H$D1.3$V_K$D1.3, a gene coding for the Fv fragment had been inserted between HindIII and EcoRI of pUC19. The sequence of this HindIII-EcoRI insert is described in the SEQ ID NO: 26.

(1-1) Plasmid pFv-PP

The plasmid pSW1$V_H$D1.3$V_K$D1.3 was digested with restriction enzymes HindIII and SmaI and separated by agarose gel electrophoresis. Thus a DNA fragment of about 470 bp containing the $V_H$ gene was extracted and purified. This DNA fragment was inserted between the HindIII and SmaI sites of a plasmid pTZ19R (manufactured by Pharmacia) to thereby give a plasmid T19VH. Separately, the plasmid pSW1$V_H$D1.3$V_K$D1.3 was digested with restriction enzymes EcoRI and SmaI and separated by agarose gel electrophoresis. Thus a DNA fragment of about 450 bp containing the $V_L$ gene was extracted and purified. This DNA fragment was inserted between the EcoRI and SmaI sites of a plasmid pTZ18R (manufactured by Pharmacia) to thereby give a plasmid T18VL. By using this plasmid T18VL as a template, PCR was effected with the use of a primer VL3' SalI having the restriction enzyme EcoRI recognition sequence represented by the SEQ ID NO: 27 and an SalI recognition sequence and a primer UPMCS corresponding to a sequence originating in pTZ18R represented by the SEQ ID NO: 28. Then the DNA thus amplified was digested with restriction enzymes HindIII and EcoRI. After separating by agarose gel electrophoresis, a HindIII, EcoRI fragment was extracted and purified.

This DNA fragment was inserted between the HindIII and EcoRI sites of the plasmid pTZ18R to thereby give a plasmid T18VLS. This plasmid T18VLS has a restriction enzyme SalI recognition sequence in the 3'-terminal side of the V1 gene.

This plasmid T18VLS was digested with restriction enzymes EcoRI and SmaI and separated by agarose gel electrophoresis. Thus a DNA fragment of about 430 bp containing the $V_L$ gene was extracted and purified. This DNA fragment was inserted between the EcoRI and SmaI sites of the plasmid T19VH having the $V_H$ gene which had been previously constructed. Thus a plasmid T19VHVLS was obtained. This plasmid T19VHVLS has the $V_H$ and $V_L$ genes in the downstream of the pTZ19Rlac promoter.

Next, by using a plasmid pEZZ18 (manufactured by Pharmacia) as a template, DNA amplification was effected by the PCR method with the use of a primer ProA5' having a restriction enzyme SalI recognition sequence represented by the SEQ ID NO: 29 and another primer ProA3' having a restriction enzyme EcoRI recognition sequence represented by the SEQ ID NO: 30.

The DNA thus amplified, which contained a gene (SEQ ID NO: 18) coding for a polypeptide containing two Fc binding domain-like structures of protein A, was digested with restriction enzymes SalI and EcoRI and subjected to agarose gel electrophoresis. Thus a DNA fragment of about 390 bp was extracted and purified. This DNA fragment was inserted between the SalI and EcoRI sites of pTZ18R to thereby give a plasmid T18PA. Subsequently, this plasmid T18PA was digested with restriction enzymes SalI and EcoRI and subjected to agarose gel electrophoresis. Thus a DNA fragment of about 390 bp was extracted and purified.

This DNA fragment was inserted between the SalI and EcoRI sites of the plasmid T19VHVLS which had been previously obtained to thereby construct a plasmid pFv-PP.

This plasmid pFv-PP codes for a fused polypeptide which contains the $V_H$ fragment and the $V_L$ fragment having two Fc binding domain-like structures of protein A (58 amino acid residues of SEQ ID NO: 31) at the C-terminus thereof.

(1-2) Construction of plasmid pM13Fv

By using a plasmid M13mp18 (manufactured by Takara Shuzo Co., Ltd.) as a template, a DNA coding for the C-terminal polypeptide of cpIII was amplified by the PCR method with the use of a primer cpIII5'-1 having a restriction enzyme SalI recognition sequence represented by the SEQ ID NO: 32 and another primer cpIII3' having a restriction enzyme SalI recognition sequence and an NheI recognition sequence represented by the SEQ ID NO: 33. This DNA was digested with a restriction enzyme SalI and subjected to agarose gel electrophoresis. Thus a DNA fragment of about 650 bp was extracted and purified. This DNA fragment was inserted into the SalI site of the plasmid pFv-PP obtained in the above Referential example B (1-1). Among the plasmids thus obtained, one in which the sequence originating in the primer cpIII5'-1 had been inserted following the $V_L$ gene in such a direction as to be ligated therewith was referred to as a plasmid pM13Fv.

This plasmid pM13Fv has been constructed in such a manner as to express a fused polypeptide wherein the $V_H$ fragment is ligated with the $V_L$ fragment having ΔcpIII coded for by the gene represented by the SEQ ID NO: 17 in the sequence listing at the C-terminus.

FIG. 1 is a schematic illustration of a DNA fragment inserted between the HindIII and EcoRI sites of the plasmid pM13Fv. The DNA sequence thereof is represented by the SEQ ID NO: 16 in the sequence listing. This plasmid pM13Fv can be easily converted into the plasmid pFv-PP constructed in the above Referential example B (1-1) by digesting with a restriction enzyme SalI and subjecting to self ligation. An *Escherichia coli* JM109 strain having this plasmid pM13Fv introduced thereinto was named *Escherichia coli* JM109/pM13Fv. This strain was deposited on Jun. 22, 1993 at National Institute of Bioscience and Human-Technology Agency of Industrial Science and Technology (1-3 Higashi 1 chome Tsukuba-shi Ibaraki-ken 305, JAPAN) in accordance with the Budapest Treaty under the accession number FERM BP-4968.

[BRIEF DESCRIPTION OF THE DRAWING]

FIG. 1 is a schematic illustration of a DNA fragment inserted between the HindIII and EcoRI sites of the plasmid pM13Fv.

[FIG. 2] FIG. 2 is a graph showing the survival ratio of a group infected with influenza A type virus.

[EXAMPLES]

Figure 1:
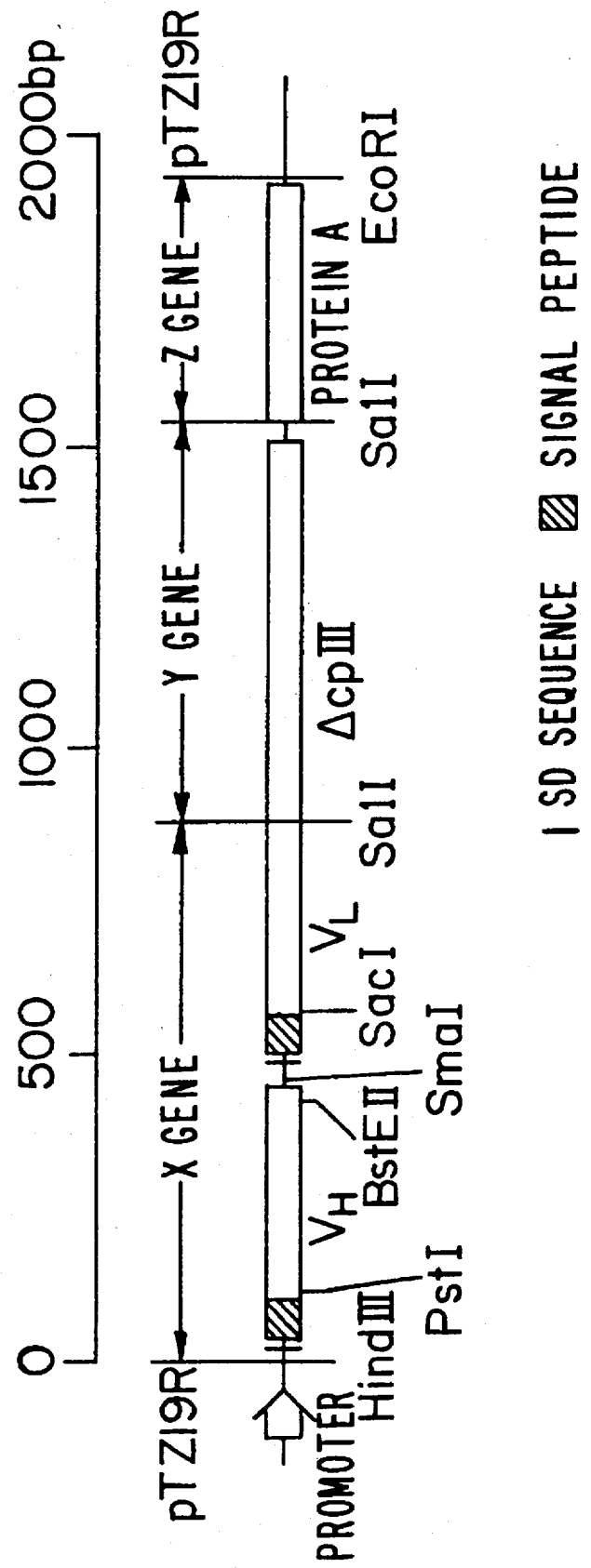
[FIG. 1]

To further illustrate the present invention in greater detail, and not byway of limitation, the following Examples will be given.

Example 1

Cloning of a DNA which Codes for the Variable Region of a Mouse Monoclonal Antibody Against Human Influenza A Type Virus A DNA which codes for the variable region of a mouse monoclonal antibody against human influenza A type virus was cloned as below:

(1) Preparation of full RNA

The full RNA was prepared from C179-producing hybridomas (FERM BP-4517) in accordance with the method of Chirgwin et al., *Biochemistry*, 18, 5294 (1979). Namely, about $1 \times 10^7$ C179-producing hybridomas were added to 20 ml of 4M guanidine thiocyanate (manufactured by Fluka) and injection and suction were repeated 5 times by using a syringe to thereby solubilize the cells. After the completion of the solubilization, the cell extract was layered over a 5.3M solution of cesium chloride and centrifuged to thereby precipitate RNA. The RNA precipitate was dissolved in a buffer solution, treated successively with phenol and chloroform and precipitated from ethanol. Thus RNA was recovered to thereby give the full RNA.

(2) Synthesis of single-stranded cDNA

By using a DNA synthesis kit (manufactured by Amersham) in accordance with the Gubler-Hoffman method, a single-stranded cDNA was synthesized with the use of about 5 μg of the full RNA prepared above and 0.5 μg of an oligo d(T) primer. The obtained cDNA was used in the amplification of a gene coding for mouse $V_H$ by the PCR method. The synthesis of the cDNA was effected at 42° C. for 120 minutes and, after the completion of the reaction, 2 μl of RNaseA (400 μg/ml) was added thereto and reacted at 37° C. for 20 minutes.

(3) Amplification of gene coding for $V_H$ by PCR method

The PCR method was carried out with the use of Gene-Amp™ PCR System 9600 (manufactured by Perkin-Elmer).

(a) The primers used in the PCR method were an oligonucleotide primer represented by the SEQ ID NO: 11 (being hybridizable with the mouse heavy chain leader sequence) and another oligonucleotide primer represented by the SEQ ID NO: 12 (being hybridizable with the mouse heavy chain constant ration).

First, 100 μl of a PCR solution containing 10 μl of a PCR buffer solution comprising 10 mM of Tris-HCl (pH 8.3), 50 mM of KCl, 0.1 mM of dATP, 0.1 mM of dGTP, 0.1 mM of dCTP, 0.1 mM of dTTP and 1.5 mM of $MgCl_2$, 1 μl of 2.5 U DNA polymerase AmpliTaq (manufactured by Perkin-Elmer Cetus), 2.5 μl portions of 10 pmol oligonucleotide primers represented by the SEQ ID NO: 11 and 12, 1 μl of the single-stranded cDNA described in Example 1-(2) and 83 μl of $H_2O$ was maintained at an initial temperature of 94° C. for 1 minute.

Next, it was heated at 94° C. for 1 minute, at 50° C. for 2 minutes and at 72° C. for 3 minutes in this order. After repeating this heating cycle 35 times, the reaction mixture was further maintained at 72° C. for 10 minutes.

(b) Purification of PCR product

The DNA product thus amplified by the PCR method as described above was separated by agarose gel electrophoresis with the use of agarose (manufactured by FMC Bio Products). From an agarose piece containing a DNA fragment of about 550 bp, the target DNA was purified by using Suprec™-01 (a centrifuging tube provided with a filter for recovering DNA: manufactured by Takara Shuzo Co., Ltd.).

(c) Ligation of DNA and transformation

About 0.2 μg of the DNA fragment of about 550 bp thus prepared was ligated to about 0.1 μg of a plasmid pT7 blue T-vector with the use of a DNA ligation kit (manufactured by Takara Shuzo Co., Ltd.).

Next, 7 μl of the above-mentioned ligation mixture was added to 200 μl of competent cells of E. coli JM109 and these cells were allowed to stand on ice for 30 minutes, at 42° C. for 1 minute and then on ice again for 1 minute. Subsequently 800 μl of an SOC medium [Molecular Cloning, A Laboratory Manual, Sambrook et al., Cold Spring Harbor Laboratory Press (1989)] was added and the resulting mixture was incubated at 37° C. for 1 hour. Then these E. coli cell were inoculated onto an L-broth agar medium containing 50 μg/ml of ampicillin, 0.1 mM of isopropyl-β-D-thiogalactopyranoside (IPTG: manufactured by Takara Shuzo Co., Ltd.) and 40 μg/ml of 5-bromo-4-chloro-3-indolyl-β-D-galactoside. After incubating at 37° C. overnight, white colonies of E. coli on the plate were selected to thereby give a transformant.

This transformant was incubated in 5 ml of the L-broth medium containing 50 μg/ml of ampicillin at 37° C. overnight. From this culture, a plasmid DNA was prepared in accordance with the alkali method (Molecular Cloning, A laboratory Manual, cited above). The plasmid thus obtained was named pC179H.

(4) Synthesis of double-stranded cDNA coding for $V_L$ (a) By using a cDNA synthesis kit in accordance with the Gubler-Hoffman method, a double-stranded cDNA was synthesized with the use of about 5 μg of the full RNA prepared by the same method as the one described in the above Example 1-(2) and an oligonucleotide primer represented by the SEQ ID NO: 13 (employed as a 3'-terminal primer). The oligonucleotide primer represented by the SEQ ID NO: 13 had been preliminarily labeled with a radioisotope $\gamma$-$^{32}$PdATP by using MEGALABEL™ (a DNA 5'-terminal labeling kit: manufactured by Takara Shuzo Co., Ltd.).

(b) Purification of double-stranded cDNA synthesis product

The double-stranded cDNA synthesized by using the cDNA synthesis kit in the above step was separated by agarose gel electrophoresis with the use of agarose (manufactured by FMC Bio Products). This gel was subjected to autoradiography and a double-stranded cDNA of about 400 bp was purified from an agarose piece containing a signal DNA fragment of about 400 bp with the use of Suprec-01.

(c) Ligation of DNA and transformation

About 0.2 μg of the DNA fragment of about 400 bp, which had been obtained in the above step in accordance with the method of Example 1-(3)-(c), was ligated to the blunt end of about 0.1 μg of pGEM-4ZDNA, which had been prepared by digesting a plasmid pGEM-4ZDNA with HincII, and this plasmid was integrated into E. coli JM109. After incubating, a transformant and a plasmid DNA were prepared. The plasmid thus obtained was named plasmid pC179L.

Example 2

Determination of DNA Sequence of Variable Region (a) 100 μg of C179 prepared by the method described in the above Referential example A-2-(3) was denatured by heating at 95° C. for 5 minutes in a buffer solution containing 2% of SDS in the presence of 0.7M of 2-mercaptoethanol. Next, the sample denatured with SDS was electrophoresed on a 12% polyacrylamide gel. After the completion of the electrophoresis, the gel was immersed in a tris-ε-amino-n-caproic acid buffer solution (pH 9.2) containing 10% of methanol and 0.1% of SDS. After shaking at room temperature for 15 minutes, it was transcribed onto a PVDF membrane (manufactured by Millipore) with the use of a semidry blotter (manufactured by Sartorius). After the completion of the transcription, the PVDF membrane was stained with a 0.1% solution of CBB and discolored with 60% methanol. Then the stained spots of proteins corresponding respectively to the H chain and the L chain were excised therefrom and dried at room temperature.

(b) The amino acid sequences were analyzed by the automated Edman method by using a gas phase sequencer PSQ1 (manufactured by Shimadzu Corporation). Each PVDF membrane piece obtained in the above step was inserted into a reaction cartridge of the sequencer and the Edman degradation was effected by using the standard program attached to PSQ1. The PTH-derivative formed by the Edman degradation was analyzed and identified by the on-line method with the use of a PTH-amino acid analyzing system PTH1.

The N-terminal amino acid sequences of the heavy chain and light chain of C179 are described respectively in the SEQ ID NO: 14 and 15.

The yield of each PTH amino acid obtained by analyzing the N-terminal amino acid sequence of the heavy chain corresponded to about 10% of the yield of the PTH amino acid in the light chain. Thus it was estimated that the amino groups in the heavy chain N-terminal Glu were mostly blocked.

(2) Determination of base sequence of DNA

The cDNA sequences coding regions in the above-mentioned plasmids pC179H and pC179L were determined by using a BcaBEST™ dideoxy sequencing kit (manufactured by Takara Shuzo Co., Ltd.). First, about 3 μg of each plasmid obtained above was denatured with 0.2N NaOH and then annealed with a primer for sequencing. Then it was labeled with $^{32}$P-dCTP in accordance with the indication of the kit.

Next, the labeled DNA was electrophoresed on a 6% polyacrylamide gel. Then the gel was dried and subjected to autoradiography to thereby determine the DNA sequence.

The cDNA sequences coding regions of these plasmids are described in the SEQ ID NO: 3 and 4 respectively.

The amino acid sequence ranging from the N-terminal Glu to Leu 18 in the heavy chain represented by the SEQ ID NO: 14 completely agreed with the amino acid sequence coded for by the DNA sequence of the base No. 1 to 54 of the gene represented by the SEQ ID NO: 3. Thus it has been proved that the plasmid pC179H is a plasmid which contains a gene coding for mouse $V_H$. The amino acid sequence coded for by the $V_H$ gene contained in this plasmid pC179H is described in the SEQ ID NO: 1.

Next, the amino acid sequence ranging from the N-terminal Asp to Ala 13 in the light chain represented by the SEQ ID NO: 15 completely agreed with the amino acid sequence coded for by the DNA sequence of the base No. 1 to 39 of the gene represented by the SEQ ID NO: 4. Thus it has been proved that the plasmid pC179L is a plasmid which contains a gene coding for mouse $V_L$. The amino acid sequence coded for by the $V_L$ gene contained in this plasmid pC179L is described in the SEQ ID NO: 2.

Thus the full amino acid sequences of $V_H$ and $V_L$ represented respectively by the SEQ ID NO: 1 and 2 have been determined and DNAs coding for these amino acid sequences are provided by the present invention.

Example 3

Determination of CDR

The whole structures of the variable regions of the heavy and light chains are similar to each other. Namely, each complementarity-determining region is composed of 4 framework regions which are ligated to each other with 3 hypervariable regions, i.e., CDRs. The amino acid sequences of the framework regions have been relatively well conserved, while the amino acid sequences of CDRs are liable to undergo mutation [Kabat, E. A., et al., Sequences of Proteins of Immunological Interest, US Department of Health and Human Services (1983)].

Based on these facts, the amino acid sequences (SEQ ID NO: 1 and 2) of the variable regions of mouse monoclonal antibody against human influenza A type virus were examined with the use of the data base of amino acid sequences of antibodies prepared by Kabat et al. as described above to thereby examine the homology. As a result, the amino acid sequences of the CDRs were identified as those represented by the SEQ ID NO: 5 to 10.

That is to say, the SEQ ID NO: 5, 6, 7, 8, 9 and 10 show respectively the amino acid sequences of CDR1 of $V_H$, CDR2 of $V_H$, CDR3 of $V_H$, CDR1 of $V_L$, CDR2 of $V_L$, CDR3 of $V_L$. Thus the amino acid sequences of CDRs of $V_H$ and $V_L$ have been identified and DNAs coding for these amino acids are provided by the present invention.

Example 4

Expression of Cloned cDNA

As a plasmid for Fv expression, the plasmid pFv-PP described in the above Referential example B may be cited. This plasmid has the PstI and SmaI sites, into which the DNA coding for $V_H$ is to be integrated, and the SacI and SalI sites, into which the DNA coding for $V_L$ is to be integrated. In order to replace the $V_H$ gene and the $V_L$ gene, which had been prepared respectively from the plasmids pC179H and pC179L obtained in Example 1, by the $V_H$ gene and the $V_L$ gene in the plasmid pFv-PP respectively followed by the ligation, the PstI site was introduced into the upstream terminus of the $V_H$ gene obtained from the plasmid pC179H and the SmaI site was introduced into the downstream terminus thereof by the PCR method. Further, the SacI site was introduced into the upstream terminus of the $V_L$ gene obtained from the plasmid pC179L and the SalI site was introduced into the downstream terminus thereof by the PCR method.

Namely, a $V_H$ forward primer for the PstI site introduction represented by the SEQ ID NO: 19, a $V_L$ backward primer for the SmaI site introduction represented by the SEQ ID NO: 20, a $V_L$ forward primer for the SacI site introduction represented by the SEQ ID NO: 21 and a $V_L$ backward primer for the SalI site introduction represented by the SEQ ID NO: 22 were designed and synthesized.

Next, PCR was effected in accordance with the method described in Example 1-(3)-(a). Namely, 100 µl of a PCR solution containing 1 µl of the plasmid pC179H (10 µg/,µl), 2.5 µl portions of the primers (20 pmol/µl) represented by the SEQ ID NO: 19 and 20, 10 µl of a PCR buffer solution, 1 µl of 2.5 U DNA polymerase AmpliTaq and 83 µl of $H_2O$ was subjected to PCR for 25 cycles with each cycle consisting of 30 seconds at 94° C., 1 minute at 55° C. and 3 minutes at 72° C. to thereby amplify the $V_H$ insert to be integrated into the plasmid pFv-PP.

Similarly, PCR was effected in the same manner with the use of the plasmid pC179L and the primers represented by the SEQ ID NO: 21 and 22 to thereby amplify the $V_L$ insert to be integrated into the plasmid pFv-PP.

Each PCR amplification product was cleaved with PstI, SmaI and SacI and SalI and electrophoresed on an agarose gel. Then the gel pieces were excised and purified by Suprec-01 to thereby prepare the $V_H$ and $V_L$ inserts.

Next, the plasmid pFv-PP was cleaved with PstI and SmaI and electrophoresed on an agarose gel. The gel piece corresponding to the plasmid was excised and purified by Suprec-01. Into the purified plasmid was inserted the $V_H$ insert. Then this plasmid was propagated in an *Escherichia coli* BMH71-18 strain. Then the plasmid was prepared from the clone by the alkali extraction method and the plasmid thus obtained was cleaved with SacI and SalI. Subsequently, this plasmid was electrophoresed on an agarose gel and the gel piece corresponding to the plasmid was excised and purified by Suprec-01. Into the purified plasmid was inserted the $V_L$ insert. Then this plasmid was propagated in an *Escherichia coli* BMH71-18 strain to thereby give clone. Next, a plasmid was prepared from the clone and the DNA sequences of the $V_H$ and $V_L$ inserts were analyzed, thus confirming that no error had occurred during the amplification by the PCR methods. The plasmid capable of expressing Fv of C179 was named plasmid T19C179FvproA. The *E. coli* BME71-18 strain transformed by this plasmid was named *Escherichia coli* BMH71-18/T19C179FvproA.

This transformant expresses the fused polypeptide of C179 with two Fc binding domain-like structures of protein A (hereinafter referred to simply as C179Fv-PP). The DNA sequence coding for C179Fv-PP is described in the SEQ ID NO: 34.

In the DNA sequence represented by the SEQ ID NO: 34, the part of the base no. 106 to 465 is a sequence coding for $V_H$, while the part of the base no. 601 to 902 is a sequence coding for $V_L$. Further, the parts of the base no. 928 to 1101 and 1102 to 1275 are sequences coding respectively for the Fc binding domain-like structures of protein A.

The C179Fv-PP thus expressed can be easily purified with IgG-Sepharose 6FF. Also, it can be converted into a plasmid, which expresses exclusively Fv of C179, by introducing a stop codon after the $V_L$ insert of the plasmid T19C179FvproA by the site-specific mutation method.

(2) Construction of scFv expression plasmid

A plasmid for scFv expression was constructed by introducing a linker between the $V_H$ insert and the $V_L$ insert in the following manner.

(a) Preparation and purification of $V_H$ insert for scFv

A primer for the introduction of a linker represented by the SEQ ID NO: 23 was designed and synthesized.

By using this primer and the above-mentioned primer for PstI site introduction represented by the SEQ ID NO: 19 and employing the plasmid pC179H as a template, the PCR amplification of the $V_H$ insert for scFv was effected. Namely, 100 µl of a PCR solution containing 1 µl of the plasmid pC179H (10 µg/µl), 5 µl portions of the primers (20 pmol/µl) represented by the SEQ ID NO: 19 and 23 respectively, 10 µl of a PCR buffer, 1 µl of 2.5 U DNA polymerase AmpliTaq and 78 µl of $H_2O$ was subjected to PCR for 25 cycles with each cycle consisting of 30 seconds at 94° C., 1 minute at 55° C. and 1 minute at 72° C. to thereby amplify the $V_H$ insert for scFv.

(b) Purification and fragmentation of PCR product

The DNA product thus amplified by the PCR method in the above step was recovered by precipitating from ethanol. Next, the DNA precipitate was digested with 10 U of restriction enzymes PstI and BamHI at 37° C. for 4 hours. The DNA fragments thus formed were separated by agarose gel electrophoresis.

From an agarose piece containing a DNA fragment of about 350 bp, the target DNA fragment was purified by using Suprec-01.

(c) Preparation and purification of linker for scFv

Oligonucleotides for synthesizing linkers represented by the SEQ ID NO: 24 and 25 were designed and synthesized. Then 200 pmol portions of these oligonucleotides were added and reacted at 65° C. for 5 minutes. Then they were slowly annealed at room temperature and were blunted by using a DNA blunting kit (manufactured by Takara Shuzo Co., Ltd.). Next, the DNA solution was digested with 10 U of PstI and SacI at 37° C. for 4 hours and the DNA fragments thus formed were separated by agarose gel electrophoresis. From an agarose piece containing a DNA fragment of about 60 bp, the target DNA fragment was purified by using Suprec-01.

(d) Construction of scFv expression plasmid

Into the plasmid part prepared by digesting the above-mentioned plasmid T19C179FvproA with PstI and SacI was inserted the above-mentioned linker for scFv by using a DNA ligation kit. Further, the plasmid having the linker for scFv inserted thereinto was propagated in an *Escherichia coli* BMH71-18 strain. From the clone thus obtained, a plasmid was prepared by the alkali extraction method. Thus 2 µg of a plasmid having the linker for scFv inserted thereinto was prepared. Next, into the plasmid part prepared by digesting this plasmid with PstI and BamHI was inserted the above-mentioned $V_H$ insert scFv by using a DNA ligation kit. Further, an *Escherichia coli* BMH71-18 strain was transformed by this plasmid and the obtained transformant was propagated to thereby give a clone. From the clone thus obtained, a plasmid was prepared. Then the DNA sequences of the $V_H$ insert for scFv, the linker for scFv and the $V_L$ insert were examined and thus it was confirmed that no error had occurred during the amplification by the PCR method or the introduction of the linkers. This plasmid capable of expressing scFv of C179 was named plasmid T19C179ScFVproA. The *Escherichia coli* BMH71-18 strain transformed by this plasmid was named *Escherichia coli* BMH71-18/T19C179ScFVproA This deposit was deposited on Feb. 28, 1994 at National Institute of Bioscience and Human-Technology Agency of Industrial Science and Technology (1-3, Higashi 1 chome Tsukuba-shi Ibaraki-ken 305, JAPAN) in accordance with the Budapest Treaty under the accesion number FERM BP-4969.

The DNAs coding for the $V_H$ and $V_L$ genes and each CDR according to the present invention can be prepared from the above-mentioned plasmid T19C179ScFvproA.

(e) Expression of C179 type scFv

The transformant prepared in the above-mentioned manner was inoculated into a 2×YT medium (Molecular Cloning, A Laboratory Manual, cited above) containing 50 µg/ml of ampicillin and 0.1% of glucose and incubated under shaking at 30° C. overnight.

The culture was then inoculated into 100 ml of a 2×YT medium containing 50 µg/ml of ampicillin and 0.1% of glucose and incubated under shaking at 30° C. When the turbidity of the culture medium measured with a spectrophotometer reached an $O.D._{600}$ Of 1, IPTG was added thereto in such a manner as to give a final concentration of 1 mM and the incubation was continued under shaking at 30° C. for additional 20 hours. After the completion of the incubation, the cells were harvested by centrifugation.

Then the cells were suspended in 5 ml of a 10 mM Tris-HCl buffer solution (pH 8.0), disrupted by ultrasonication and centrifuged to thereby give the supernatant.

About 5 ml of the supernatant thus obtained was filtered successively through filters of 0.45 µm and 0.22 µm (manufactured by Millipore). To purify the scFv fragment from the filtrate, IgG Sepharose 6FF (manufactured by Pharmacia) was used.

Namely, the filtrate was slowly passed through a column packed with IgG Sepharose 6FF to thereby allow the column to adsorb the scFv fragment. After washing with a buffer solution for binding [10 mM Tris-HCl buffer solution (pH 8.0), 140 mM NaCl, 1 mM EDTA, 0.1 mM PMSF (phenylmethylsulfonyl fluoride)], the target fraction was eluted with a 50 mM glycine hydrochloride buffer solution (pH 2.5). The eluate was quickly neutralized with a 1M Tris-HCl buffer solution (pH 8.0). Thus a fused polypeptide of scFv of C179 with two Fc binding domain-like structures of protein A (hereinafter referred to simply as scFv-PP) was obtained. The DNA sequence coding for this scFv-PP is described in the SEQ ID NO: 35. In the DNA sequence represented by the SEQ ID NO: 35, the sequence of the base no. 106 to 471 is one coding for $V_H$, while the sequence of the base no. 529 to 830 is one coding for $V_L$. The sequences of the base no. 856 to 1029 and the base no. 1030 to 1203 are sequences coding respectively for the Fc binding domain-like structures of protein A. Also, it can be converted into a plasmid, which expresses exclusively scFv of C179, by introducing a stop codon after the $V_L$ insert of the plasmid T19C179FVproA by the site-specific mutation method.

Example 5

Detection of Human Influenza A Type Virus

Human influenza A type virus was detected with the scFv obtained by the present invention by the ELISA method in the following manner.

scFv-PP (10 µg/ml) having the antibody variable region of C179 expressed therein obtained in Example 4 was added in 100 µl portions into the wells of 96-well microplate (Falcon 3072; manufactured by Becton Dickinson Labware). Then the plate was maintained at 37° C. for 1 hour and 30 minutes to thereby immobilize scFv-PP onto the plate followed by the blocking with the use of a protein solution for blocking (Block Ace; manufactured by Snow Brand). After the completion of the blocking, 100 µl portions of dilutions (10 HA U/ml) of human influenza A type virus subtypes prepared by the method described in Referential Example A-1 including A/PR/8/34 (the H1N1 subtype), A/Okuda/57 (the H2N2 subtype) and A2/Aichi/2/68 (the H3N2 subtype) were added to the wells for the assay respectively. After reacting for 1 hour, these wells were washed with PBS containing 0.05% of Tween 20.

Next, 100 μl of a 500-fold dilution of anti-A/Okuda/57 serum (manufactured by Takara Shuzo Co., Ltd.) showing an affinity for human influenza A type virus was added thereto and reacted for 1 hour.

The anti-A/Okuda/57 serum was prepared in the following manner. Namely, A/Okuda/57 (5000 HA U) was suspended in Freund's complete adjuvant prior to use and intramuscularly injected into a rabbit twice at an interval of 1 month. 10 days after the second intramuscular injection, the whole blood of the animal was collected from the heart and a serum was prepared to thereby give the anti-A/Okuda/57 serum.

After washing, 100 μl of a dilution of peroxidase-labeled goat anti-rabbit immunoglobulin G solution (manufactured by Cappel) was added to the above-mentioned anti-A/Okuda/57 serum reaction mixture. After maintaining at a given temperature for 1 hour and 30 minutes, a substrate buffer solution [0.03% of $H_2O_2$, 1 mg/ml of o-phenylenediamine dihydrochloride in citrate-phosphate buffer solution (pH 5.2)] was added thereto and thus the peroxidase reaction was effected at room temperature for 5 minutes. Then the reaction was ceased by adding 2M sulfuric acid and the absorbance at 492 nm was measured. Thus the affinity of scFv-PP for each subtype was assayed. Table 2 shows the results. The abovementioned assay of affinity and the control test were effected each in 3 runs. The absorbances at 492 nm listed in Table 2 are each the mean.

TABLE 2

| Virus . Subtype | Absorbance at 492 nm |
|---|---|
| H1N1 | 0.150 |
| H2N2 | 0.303 |
| H3N2 | 0.074 |
| Control | 0.074 |

As Table 2 clearly shows, the scFv obtained by the present invention shows avidities for the H1N1 and H2N2 subtypes but not for the H3N2 subtype. Accordingly, the scFv-PP obtained by the present invention is useful in the detection and typing of human influenza A type virus.

[EFFECTS OF THE INVENTION]

According to the present invention, genes which recognize the H1N1 and H2N2 subtypes of human influenza A type virus in common and code for the variable region and CDRs of a monoclonal antibody having a neutralization activity against this virus have been specified. These genes are useful in the production of various artificial antibodies and antigen-binding polypeptides through genetic engineering techniques. Further, the artificial antibodies and polypeptides thus obtained are useful in the diagnosis and treatment of human influenza.

We claim:

1. An isolated DNA coding for the variable region of an anti-human influenza A type virus antibody, said antibody having the following characteristics (a) and (b):

(a) specifically binds to the stem region of haemaggulutinin molecule of H1N1 and H2N2 subtypes of human influenza A type virus but does not specifically bind to the stem region of haemaggulutinin molecule of H3N2 subtype; and (b) has a neutralization activity for the H1N1 and H2N2 subtypes of human influenza A type virus but no neutralization activity for the H3N2 subtype.

2. The isolated DNA as claimed in claim 1, wherein said variable region of the anti-human influenza A type virus antibody has the amino acid sequence shown in the SEQ ID NOS: 1 and 2.

3. The isolated DNA as claimed in claim 2, wherein said DNA has the nucleic acid sequence shown in the SEQ ID NOS: 3 and 4.

4. The isolated DNA as claimed in claim 1, which is hybridizable with the DNA shown in the SEQ ID NOS: 3 and 4 under stringent hybridization conditions.

5. The isolated DNA as claimed in claim 1, wherein said variable region of the anti-human influence A type virus antibody comprises a complementary-determining region having the amino acid sequence shown in the SEQ ID NOS: 5, 6, 7, 8, 9 and 10.

* * * * *

SEQUENCE LISTING ( 1 ) GENERAL INFORMATION:

( i i i ) NUMBER OF SEQUENCES: 36

( 2 ) INFORMATION FOR SEQ ID NO:1:

( i ) SEQUENCE CHARACTERISTICS:
    ( A ) LENGTH: 116
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:1:

```
Glu Val Lys Leu Val Glu Ser Gly Gly Gly Leu Val Gln Pro Gly
  1               5                  10                  15

Gly Ser Leu Arg Leu Ser Cys Gly Thr Ser Gly Phe Thr Leu Thr
                 20                  25                  30

Asp Asp Tyr Met Thr Trp Val Arg Gln Pro Pro Gly Lys Ala Leu
                 35                  40                  45

Glu Trp Leu Gly Phe Ile Arg Asp Arg Ala Asn Gly Tyr Thr Thr
                 50                  55                  60

Glu Tyr Ser Ala Ser Val Lys Gly Arg Phe Thr Ile Ser Arg Asp
                 65                  70                  75

Asn Ser Gln Ser Ile Val Tyr Leu Gln Met Asn Thr Leu Arg Val
                 80                  85                  90

Glu Asp Ser Ala Thr Tyr Tyr Cys Ala Arg Pro Lys Gly Tyr Phe
                 95                 100                 105

Pro Tyr Ala Met Asp Tyr Trp Gly Gln Gly Thr
                110                 115
```

( 2 ) INFORMATION FOR SEQ ID NO:2:

( i ) SEQUENCE CHARACTERISTICS:
    ( A ) LENGTH: 96
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:2:

```
Asp Ile Gln Met Thr Gln Ser Pro Ala Ser Gln Ser Ala Ser Leu
 1               5                  10                  15

Gly Glu Ser Val Thr Ile Thr Cys Leu Ala Ser Gln Thr Ile Gly
                20                  25                  30

Thr Trp Leu Ala Trp Tyr Gln Gln Lys Pro Gly Lys Ser Pro Gln
                35                  40                  45

Leu Leu Ile Tyr Ala Ala Thr Ser Leu Ala Asp Gly Val Pro Ser
                50                  55                  60

Arg Phe Ser Gly Ser Gly Ser Gly Thr Lys Phe Ser Phe Lys Ile
                65                  70                  75

Ser Ser Leu Gln Ala Glu Asp Phe Val Ser Tyr Tyr Cys Gln Gln
                80                  85                  90

Leu Tyr Ser Thr Pro Trp Thr Phe
                95
```

( 2 ) INFORMATION FOR SEQ ID NO:3:

( i ) SEQUENCE CHARACTERISTICS:
    ( A ) LENGTH: 347
    ( B ) TYPE: nucleic acid
    ( C ) STRANDEDNESS: double
    ( D ) TOPOLOGY: linear ( i i ) MOLECULE TYPE: cDNA to mRNA ( x i ) SEQUENCE DESCRIPTION: SEQ ID NO:3:

```
GAG GTG AAG CTG GTG GAG TCT GGA GGA GGC TTG GTA CAG CCT GGG    45
Glu Val Lys Leu Val Glu Ser Gly Gly Gly Leu Val Gln Pro Gly
 1               5                  10                  15

GGT TCT CTG AGA CTC TCC TGT GGA ACT TCT GGA TTC ACC CTC ACT    90
Gly Ser Leu Arg Leu Ser Cys Gly Thr Ser Gly Phe Thr Leu Thr
                20                  25                  30

GAT GAC TAC ATG ACC TGG GTC CGC CAG CCT CCA GGA AAG GCA CTT   135
Asp Asp Tyr Met Thr Trp Val Arg Gln Pro Pro Gly Lys Ala Leu
                35                  40                  45

GAG TGG TTG GGT TTT ATT AGA GAC AGA GCT AAT GGT TAC ACA ACA   180
Glu Trp Leu Gly Phe Ile Arg Asp Arg Ala Asn Gly Tyr Thr Thr
                50                  55                  60

GAG TAC AGT GCA TCT GTG AAG GGT CGG TTC ACC ATC TCC AGA GAT   225
Glu Tyr Ser Ala Ser Val Lys Gly Arg Phe Thr Ile Ser Arg Asp
                65                  70                  75

AAT TCC CAA AGC ATC GTC TAT CTT CAA ATG AAC ACC CTG AGA GTT   270
Asn Ser Gln Ser Ile Val Tyr Leu Gln Met Asn Thr Leu Arg Val
                80                  85                  90

GAG GAC AGT GCC ACT TAT TAC TGT GCA AGG CCC AAA GGC TAC TTT   315
Glu Asp Ser Ala Thr Tyr Tyr Cys Ala Arg Pro Lys Gly Tyr Phe
                95                 100                 105

CCC TAT GCT ATG GAC TAC TGG GGT CAA GGA AC                    347
Pro Tyr Ala Met Asp Tyr Trp Gly Gln Gly
                110                 115
```

( 2 ) INFORMATION FOR SEQ ID NO:4:

(i) SEQUENCE CHARACTERISTICS:
    (A) LENGTH: 295
    (B) TYPE: nucleic acid
    (C) STRANDEDNESS: double
    (D) TOPOLOGY: linear (ii) MOLECULE TYPE: mRNA to cDNA (xi) SEQUENCE DESCRIPTION: SEQ ID NO:4:

| GAC | ATT | CAG | ATG | ACC | CAG | TCT | CCT | GCC | TCC | CAG | TCT | GCA | TCT | CTG | 45 |
|---|---|---|---|---|---|---|---|---|---|---|---|---|---|---|---|
| Asp | Ile | Gln | Met | Thr | Gln | Ser | Pro | Ala | Ser | Gln | Ser | Ala | Ser | Leu | |
| 1 | | | | 5 | | | | | 10 | | | | | 15 | |

| GGA | GAA | AGT | GTC | ACC | ATC | ACA | TGC | CTG | GCA | AGT | CAG | ACC | ATT | GGT | 90 |
|---|---|---|---|---|---|---|---|---|---|---|---|---|---|---|---|
| Gly | Glu | Ser | Val | Thr | Ile | Thr | Cys | Leu | Ala | Ser | Gln | Thr | Ile | Gly | |
| | | | | 20 | | | | | 25 | | | | | 30 | |

| ACA | TGG | TTA | GCA | TGG | TAT | CAG | CAG | AAA | CCA | GGG | AAA | TCT | CCT | CAG | 135 |
|---|---|---|---|---|---|---|---|---|---|---|---|---|---|---|---|
| Thr | Trp | Leu | Ala | Trp | Tyr | Gln | Gln | Lys | Pro | Gly | Lys | Ser | Pro | Gln | |
| | | | | 35 | | | | | 40 | | | | | 45 | |

| CTC | CTG | ATT | TAT | GCT | GCA | ACC | AGC | TTG | GCA | GAT | GGG | GTC | CCA | TCA | 180 |
|---|---|---|---|---|---|---|---|---|---|---|---|---|---|---|---|
| Leu | Leu | Ile | Tyr | Ala | Ala | Thr | Ser | Leu | Ala | Asp | Gly | Val | Pro | Ser | |
| | | | | 50 | | | | | 55 | | | | | 60 | |

| AGG | TTC | AGT | GGT | AGT | GGA | TCT | GGC | ACA | AAA | TTT | TCC | TTC | AAG | ATC | 225 |
|---|---|---|---|---|---|---|---|---|---|---|---|---|---|---|---|
| Arg | Phe | Ser | Gly | Ser | Gly | Ser | Gly | Thr | Lys | Phe | Ser | Phe | Lys | Ile | |
| | | | | 65 | | | | | 70 | | | | | 75 | |

| AGC | AGC | CTA | CAG | GCT | GAA | GAT | TTT | GTA | AGT | TAT | TAC | TGT | CAA | CAA | 270 |
|---|---|---|---|---|---|---|---|---|---|---|---|---|---|---|---|
| Ser | Ser | Leu | Gln | Ala | Glu | Asp | Phe | Val | Ser | Tyr | Tyr | Cys | Gln | Gln | |
| | | | | 80 | | | | | 85 | | | | | 90 | |

| CTT | TAC | AGT | ACT | CCG | TGG | ACG | TTC | G | | | | | | | 295 |
|---|---|---|---|---|---|---|---|---|---|---|---|---|---|---|---|
| Leu | Tyr | Ser | Thr | Pro | Trp | Thr | Phe | | | | | | | | |
| | | | | 95 | | | | | | | | | | | |

(2) INFORMATION FOR SEQ ID NO:5:

(i) SEQUENCE CHARACTERISTICS:
    (A) LENGTH: 7
    (B) TYPE: amino acid
    (C) STRANDEDNESS: single
    (D) TOPOLOGY: linear (ii) MOLECULE TYPE: peptide (vi) ORIGINAL SOURCE: heavy chain of C179

(xi) SEQUENCE DESCRIPTION: SEQ ID NO:5:

| Leu | Thr | Asp | Asp | Tyr | Met | Thr |
|---|---|---|---|---|---|---|
| 1 | | | | 5 | | |

(2) INFORMATION FOR SEQ ID NO:6:

(i) SEQUENCE CHARACTERISTICS:
    (A) LENGTH: 12
    (B) TYPE: amino acid
    (C) STRANDEDNESS: single
    (D) TOPOLOGY: linear (ii) MOLECULE TYPE: peptide (vi) ORIGINAL SOURCE: heavy chain of C179

(xi) SEQUENCE DESCRIPTION: SEQ ID NO:6:

| Phe | Ile | Arg | Asp | Arg | Ala | Asn | Gly | Tyr | Thr | Thr | Glu |
|---|---|---|---|---|---|---|---|---|---|---|---|
| 1 | | | | 5 | | | | | 10 | | |

(2) INFORMATION FOR SEQ ID NO:7:

(i) SEQUENCE CHARACTERISTICS:
    (A) LENGTH: 10

( B ) TYPE: amino acid
( C ) STRANDEDNESS: single
( D ) TOPOLOGY: linear ( i i ) MOLECULE TYPE: peptide ( v i ) ORIGINAL SOURCE: heavy chain of C179

( x i ) SEQUENCE DESCRIPTION: SEQ ID NO:7:

Arg Pro Lys Gly Tyr Phe Pro Tyr Ala Met
 1               5                    10

( 2 ) INFORMATION FOR SEQ ID NO:8:

( i ) SEQUENCE CHARACTERISTICS:
        ( A ) LENGTH: 6
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE: light chain of C179

( x i ) SEQUENCE DESCRIPTION: SEQ ID NO:8:

Thr Ile Gly Thr Trp Leu
 1               5

( 2 ) INFORMATION FOR SEQ ID NO:9:

( i ) SEQUENCE CHARACTERISTICS:
        ( A ) LENGTH: 6
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE: light chain of C179

( x i ) SEQUENCE DESCRIPTION: SEQ ID NO:9:

Ala Ala Thr Ser Leu Ala
 1               5

( 2 ) INFORMATION FOR SEQ ID NO:10:

( i ) SEQUENCE CHARACTERISTICS:
        ( A ) LENGTH: 5
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE: light chain of C179

( x i ) SEQUENCE DESCRIPTION: SEQ ID NO:10:

Gln Leu Tyr Ser Thr
 1           5

( 2 ) INFORMATION FOR SEQ ID NO:11:

( i ) SEQUENCE CHARACTERISTICS:
        ( A ) LENGTH: 33
        ( B ) TYPE: nucleic acid
        ( C ) STRANDEDNESS: single
        ( D ) TOPOLOGY: linear ( i i ) MOLECULE TYPE: other nucleic acid (synthetic DNA)

( x i ) SEQUENCE DESCRIPTION: SEQ ID NO:11:

```
GGGAATTCAT GRASTTSKGG Y TMARCTKGR TTT          33
```

(2) INFORMATION FOR SEQ ID NO:12:

(i) SEQUENCE CHARACTERISTICS:
        (A) LENGTH: 20
        (B) TYPE: nucleic acid
        (C) STRANDEDNESS: single
        (D) TOPOLOGY: linear (ii) MOLECULE TYPE: other nucleic acid (synthetic DNA)

(xi) SEQUENCE DESCRIPTION: SEQ ID NO:12:

```
ARTARCCCTT GACCAGGCAT          20
```

(2) INFORMATION FOR SEQ ID NO:13:

(i) SEQUENCE CHARACTERISTICS:
        (A) LENGTH: 14
        (B) TYPE: nucleic acid
        (C) STRANDEDNESS: single
        (D) TOPOLOGY: linear (ii) MOLECULE TYPE: other nucleic acid (synthetic DNA)

(xi) SEQUENCE DESCRIPTION: SEQ ID NO:13:

```
TGGTGGGAAG ATGG          14
```

(2) INFORMATION FOR SEQ ID NO:14:

(i) SEQUENCE CHARACTERISTICS:
        (A) LENGTH: 18
        (B) TYPE: amino acid
        (C) STRANDEDNESS: single
        (D) TOPOLOGY: linear (ii) MOLECULE TYPE: peptide (vi) ORIGINAL SOURCE: heavy chain of C179

(xi) SEQUENCE DESCRIPTION: SEQ ID NO:14:

```
Glu Val Lys Leu Val Glu Ser Gly Gly Gly Leu Val Gln Pro Gly
 1               5                  10                  15

Gly Ser Leu
```

(2) INFORMATION FOR SEQ ID NO:15:

(i) SEQUENCE CHARACTERISTICS:
        (A) LENGTH: 13
        (B) TYPE: amino acid
        (C) STRANDEDNESS: single
        (D) TOPOLOGY: linear (ii) MOLECULE TYPE: peptide (vi) ORIGINAL SOURCE: light chain of C179

(xi) SEQUENCE DESCRIPTION: SEQ ID NO:15:

```
Asp Ile Gln Met Thr Gln Ser Pro Ala Ser Gln Ser Ala
 1               5                  10
```

(2) INFORMATION FOR SEQ ID NO:16:

(i) SEQUENCE CHARACTERISTICS:
        (A) LENGTH: 1952
        (B) TYPE: nucleic acid
        (C) STRANDEDNESS: double
        (D) TOPOLOGY: linear (xi) SEQUENCE DESCRIPTION: SEQ ID NO:16:

-continued

```
AAGCTTGCAT GCAAATTCTA TTTCAAGGAG ACAGTCATAA TGAAATACCT ATTGCCTACG      60
GCAGCCGCTG GATTGTTATT ACTCGCTGCC CAACCAGCGA TGGCCCAGGT GCAGCTGCAG     120
GAGTCAGGAC CTGGCCTGGT GGCGCCCTCA CAGAGCCTGT CCATCACATG CACCGTCTCA     180
GGGTTCTCAT TAACCGGCTA TGGTGTAAAC TGGGTTCGCC AGCCTCCAGG AAAGGGTCTG     240
GAGTGGCTGG GAATGATTTG GGGTGATGGA AACACAGACT ATAATTCAGC TCTCAAATCC     300
AGACTGAGCA TCAGCAAGGA CAACTCCAAG AGCCAAGTTT TCTTAAAAAT GAACAGTCTG     360
CACACTGATG ACACAGCCAG GTACTACTGT GCCAGAGAGA GAGATTATAG GCTTGACTAC     420
TGGGGCCAAG GCACCACGGT CACCGTCTCC TCATAATAAG AGCTATCCCG GGAGCTTGCA     480
TGCAAATTCT ATTTCAAGGA GACAGTCATA ATGAAATACC TATTGCCTAC GGCAGCCGCT     540
GGATTGTTAT TACTCGCTGC CCAACCAGCG ATGGCCGACA TCGAGCTCAC CCAGTCTCCA     600
GCCTCCCTTT CTGCGTCTGT GGGAGAAACT GTCACCATCA CATGTCGAGC AAGTGGGAAT     660
ATTCACAATT ATTTAGCATG GTATCAGCAG AAACAGGGAA AATCTCCTCA GCTCCTGGTC     720
TATTATACAA CAACCTTAGC AGATGGTGTG CCATCAAGGT TCAGTGGCAG TGGATCAGGA     780
ACACAATATT CTCTCAAGAT CAACAGCCTG CAACCTGAAG ATTTTGGGAG TTATTACTGT     840
CAACATTTTT GGAGTACTCC TCGGACGTTC GGTGGAGGCA CCAAGCTGGA GTCGACTCCA     900
TTCGTTTGTG AATATCAAGG CCAATCGTCT GACCTGCCTC AACCTCCTGT CAATGCTGGC     960
GGCGGCTCTG GTGGTGGTTC TGGTGGCGGC TCTGAGGGTG GTGGCTCTGA GGGTGGCGGT    1020
TCTGAGGGTG GCGGCTCTGA GGGAGGCGGT TCCGGTGGTG GCTCTGGTTC GGGTGATTTT    1080
GATTATGAAA AGATGGCAAA CGCTAATAAG GGGGCTATGA CCGAAAATGC CGATGAAAAC    1140
GCGCTACAGT CTGACGCTAA AGGCAAACTT GATTCTGTCG CTACTGATTA CGGTGCTGCT    1200
ATCGATGGTT TCATTGGTGA CGTTTCCGGC CTTGCTAATG GTAATGGTGC TACTGGTGAT    1260
TTTGCTGGCT CTAATTCCCA AATGGCTCAA GTCGGTGACG GTGATAATTC ACCTTTAATG    1320
AATAATTTCC GTCAATATTT ACCTTCCCTC CCTCAATCGG TTGAATGTCG CCCTTTTGTC    1380
TTTAGCGCTG GTAAACCATA TGAATTTTCT ATTGATTGTG ACAAAATAAA CTTATTCCGT    1440
GGTGTCTTTG CGTTTCTTTT ATATGTTGCC ACCTTTATGT ATGTATTTTC TACGTTTGCT    1500
AACATACTGC GTAATAAGGA GTCTTAATCA TGCCAGTTCT TTTGGGTGCT AGCTGTCGAC    1560
TGCGCAACAC GATGAAGCCG TAGACAACAA ATTCAACAAA GAACAACAAA ACGCGTTCTA    1620
TGAGATCTTA CATTTACCTA ACTTAAACGA AGAACAACGA AACGCCTTCA TCCAAAGTTT    1680
AAAAGATGAC CCAAGCCAAA GCGCTAACCT TTAGCAGAA GCTAAAAAGC TAAATGATGC     1740
TCAGGCGCCG AAAGTAGACA ACAAATTCAA CAAAGAACAA CAAAACGCGT TCTATGAGAT    1800
CTTACATTTA CCTAACTTAA ACGAAGAACA ACGAAACGCC TTCATCCAAA GTTTAAAAGA    1860
TGACCCAAGC CAAAGCGCTA ACCTTTTAGC AGAAGCTAAA AAGCTAAATG ATGCTCAGGC    1920
GCCGAAAGTA GACGCGAATT AGCTGGGAAT TC                                  1952
```

( 2 ) INFORMATION FOR SEQ ID NO:17:

( i ) SEQUENCE CHARACTERISTICS:
( A ) LENGTH: 630
( B ) TYPE: nucleic acid
( C ) STRANDEDNESS: double
( D ) TOPOLOGY: linear ( x i ) SEQUENCE DESCRIPTION: SEQ ID NO:17:

```
CCATTCGTTT GTGAATATCA AGGCCAATCG TCTGACCTGC CTCAACCTCC TGTCAATGCT      60
```

```
GGCGGCGGCT CTGGTGGTGG TTCTGGTGGC GGCTCTGAGG GTGGTGGCTC TGAGGGTGGC    120

GGTTCTGAGG GTGGCGGCTC TGAGGGAGGC GGTTCCGGTG GTGGCTCTGG TTCCGGTGAT    180

TTTGATTATG AAAAGATGGC AAACGCTAAT AAGGGGGCTA TGACCGAAAA TGCCGATGAA    240

AACGCGCTAC AGTCTGACGC TAAAGGCAAA CTTGATTCTG TCGCTACTGA TTACGGTGCT    300

GCTATCGATG GTTTCATTGG TGACGTTTCC GGCCTTGCTA ATGGTAATGG TGCTACTGGT    360

GATTTTGCTG GCTCTAATTC CCAAATGGCT CAAGTCGGTG ACGGTGATAA TTCACCTTTA    420

ATGAATAATT TCCGTCAATA TTTACCTTCC CTCCCTCAAT CGGTTGAATG TCGCCCTTTT    480

GTCTTTAGCG CTGGTAAACC ATATGAATTT TCTATTGATT GTGACAAAAT AAACTTATTC    540

CGTGGTGTCT TTGCGTTTCT TTTATATGTT GCCACCTTTA TGTATGTATT TTCTACGTTT    600

GCTAACATAC TGCGTAATAA GGAGTCTTAA                                    630
```

(2) INFORMATION FOR SEQ ID NO:18:

(i) SEQUENCE CHARACTERISTICS:
        (A) LENGTH: 348
        (B) TYPE: nucleic acid
        (C) STRANDEDNESS: double
        (D) TOPOLOGY: linear (xi) SEQUENCE DESCRIPTION: SEQ ID NO:18:

```
GTAGACAACA AATTCAACAA AGAACAACAA AACGCGTTCT ATGAGATCTT ACATTTACCT     60

AACTTAAACG AAGAACAACG AAACGCCTTC ATCCAAAGTT TAAAAGATGA CCCAAGCCAA    120

AGCGCTAACC TTTTAGCAGA AGCTAAAAAG CTAAATGATG CTCAGGCGCC GAAAGTAGAC    180

AACAAATTCA ACAAAGAACA ACAAAACGCG TTCTATGAGA TCTTACATTT ACCTAACTTA    240

AACGAAGAAC AACGAAACGC CTTCATCCAA AGTTTAAAAG ATGACCCAAG CCAAAGCGCT    300

AACCTTTTAG CAGAAGCTAA AAAGCTAAAT GATGCTCAGG CGCCGAAA                348
```

(2) INFORMATION FOR SEQ ID NO:19:

(i) SEQUENCE CHARACTERISTICS:
        (A) LENGTH: 30
        (B) TYPE: nucleic acid
        (C) STRANDEDNESS: single
        (D) TOPOLOGY: linear (ii) MOLECULE TYPE: other nucleic acid (synthetic DNA)

(xi) SEQUENCE DESCRIPTION: SEQ ID NO:19:

```
CGGATCCTGC AGGAGTCTGG AGGAGGCCTG    30
```

(2) INFORMATION FOR SEQ ID NO:20:

(i) SEQUENCE CHARACTERISTICS:
        (A) LENGTH: 42
        (B) TYPE: nucleic acid
        (C) STRANDEDNESS: single
        (D) TOPOLOGY: linear (ii) MOLECULE TYPE: other nucleic acid (synthetic DNA)

(xi) SEQUENCE DESCRIPTION: SEQ ID NO:20:

```
CGGATCCCGG GATAGCTCTT ATTAGACGAT GACTGAGGTT CC    42
```

(2) INFORMATION FOR SEQ ID NO:21:

(i) SEQUENCE CHARACTERISTICS:
        (A) LENGTH: 31
        (B) TYPE: nucleic acid
        (C) STRANDEDNESS: single ( D ) TOPOLOGY: linear ( i i ) MOLECULE TYPE: other nucleic acid (synthetic DNA)

( x i ) SEQUENCE DESCRIPTION: SEQ ID NO:21:

GGAATTCGAG CTCACCCAGT CTCCTGCCTC C    31

( 2 ) INFORMATION FOR SEQ ID NO:22:

( i ) SEQUENCE CHARACTERISTICS:
        ( A ) LENGTH: 35
        ( B ) TYPE: nucleic acid
        ( C ) STRANDEDNESS: single
        ( D ) TOPOLOGY: linear ( i i ) MOLECULE TYPE: other nucleic acid (synthetic DNA)

( x i ) SEQUENCE DESCRIPTION: SEQ ID NO:22:

GGAATTCTAC GTCGACTCCA GCTTGGTGCC TCCAC    35

( 2 ) INFORMATION FOR SEQ ID NO:23:

( i ) SEQUENCE CHARACTERISTICS:
        ( A ) LENGTH: 37
        ( B ) TYPE: nucleic acid
        ( C ) STRANDEDNESS: single
        ( D ) TOPOLOGY: linear ( i i ) MOLECULE TYPE: other nucleic acid (synthetic DNA)

( x i ) SEQUENCE DESCRIPTION: SEQ ID NO:23:

CCCGGATCCA CCGCCACCTG AGGAGACGAT GACTGAG    37

( 2 ) INFORMATION FOR SEQ ID NO:24:

( i ) SEQUENCE CHARACTERISTICS:
        ( A ) LENGTH: 43
        ( B ) TYPE: nucleic acid
        ( C ) STRANDEDNESS: single
        ( D ) TOPOLOGY: linear ( i i ) MOLECULE TYPE: other nucleic acid (synthetic DNA)

( x i ) SEQUENCE DESCRIPTION: SEQ ID NO:24:

CTACACTGCA GATGGATCCG GCGGTGGTGG GTCGGGTGGC GGC    43

( 2 ) INFORMATION FOR SEQ ID NO:25:

( i ) SEQUENCE CHARACTERISTICS:
        ( A ) LENGTH: 42
        ( B ) TYPE: nucleic acid
        ( C ) STRANDEDNESS: single
        ( D ) TOPOLOGY: linear ( i i ) MOLECULE TYPE: other nucleic acid (synthetic DNA)

( x i ) SEQUENCE DESCRIPTION: SEQ ID NO:25:

CCCGAGCTCG ATGTCAGATC CGCCGCCACC CGACCCACCA CC    42

( 2 ) INFORMATION FOR SEQ ID NO:26:

( i ) SEQUENCE CHARACTERISTICS:
        ( A ) LENGTH: 923
        ( B ) TYPE: nucleic acid
        ( C ) STRANDEDNESS: double
        ( D ) TOPOLOGY: linear ( x i ) SEQUENCE DESCRIPTION: SEQ ID NO:26:

AAGCTTGCAT GCAAATTCTA TTTCAAGGAG ACAGTCATAA TGAAATACCT ATTGCCTACG    60

```
GCAGCCGCTG GATTGTTATT ACTCGCTGCC CAACCAGCGA TGGCCCAGGT GCAGCTGCAG    120
GAGTCAGGAC CTGGCCTGGT GGCGCCCTCA CAGAGCCTGT CCATCACATG CACCGTCTCA    180
GGGTTCTCAT TAACCGGCTA TGGTGTAAAC TGGGTTCGCC AGCCTCCAGG AAAGGGTCTG    240
GAGTGGCTGG GAATGATTTG GGGTGATGGA AACACAGACT ATAATTCAGC TCTCAAATCC    300
AGACTGAGCA TCAGCAAGGA CAACTCCAAG AGCCAAGTTT TCTTAAAAAT GAACAGTCTG    360
CACACTGATG ACACAGCCAG GTACTACTGT GCCAGAGAGA GAGATTATAG CTTGACTAC    420
TGGGGCCAAG GCACCACGGT CACCGTCTCC TCATAATAAG AGCTATCCCG GGAGCTTGCA    480
TGCAAATTCT ATTTCAAGGA GACAGTCATA ATGAAATACC TATTGCCTAC GGCAGCCGCT    540
GGATTGTTAT TACTCGCTGC CCAACCAGCG ATGGCCGACA TCGAGCTCAC CCAGTCTCCA    600
GCCTCCCTTT CTGCGTCTGT GGGAGAAACT GTCACCATCA CATGTCGAGC AAGTGGGAAT    660
ATTCACAATT ATTTAGCATG GTATCAGCAG AAACAGGGAA AATCTCCTCA GCTCCTGGTC    720
TATTATACAA CAACCTTAGC AGATGGTGTG CCATCAAGGT TCAGTGGCAG TGGATCAGGA    780
ACACAATATT CTCTCAAGAT CAACAGCCTG CAACCTGAAG ATTTTGGGAG TTATTACTGT    840
CAACATTTTT GGAGTACTCC TCGGACGTTC GGTGGAGGCA CCAAGCTGGA AATCAAACGG    900
TAATAAGGAT CCAGCTCGAA TTC                                            923
```

(2) INFORMATION FOR SEQ ID NO:27:

(i) SEQUENCE CHARACTERISTICS:
        (A) LENGTH: 34
        (B) TYPE: nucleic acid
        (C) STRANDEDNESS: single
        (D) TOPOLOGY: linear (ii) MOLECULE TYPE: other nucleic acid (synthetic DNA)

(xi) SEQUENCE DESCRIPTION: SEQ ID NO:27:

```
GCGAATTCTA AGTCGACTCC AGCTTGGTGC CTCC    34
```

(2) INFORMATION FOR SEQ ID NO:28:

(i) SEQUENCE CHARACTERISTICS:
        (A) LENGTH: 25
        (B) TYPE: nucleic acid
        (C) STRANDEDNESS: single
        (D) TOPOLOGY: linear (ii) MOLECULE TYPE: other nucleic acid (synthetic DNA)

(xi) SEQUENCE DESCRIPTION: SEQ ID NO:28:

```
CGACGTTGTA AAACGACGGC CAGTG    25
```

(2) INFORMATION FOR SEQ ID NO:29:

(i) SEQUENCE CHARACTERISTICS:
        (A) LENGTH: 27
        (B) TYPE: nucleic acid
        (C) STRANDEDNESS: single
        (D) TOPOLOGY: linear (ii) MOLECULE TYPE: other nucleic acid (synthetic DNA)

(xi) SEQUENCE DESCRIPTION: SEQ ID NO:29:

```
GCGTCGACTG CGCAACACGA TGAAGCC    27
```

(2) INFORMATION FOR SEQ ID NO:30:

(i) SEQUENCE CHARACTERISTICS:

( A ) LENGTH: 27
( B ) TYPE: nucleic acid
( C ) STRANDEDNESS: single
( D ) TOPOLOGY: linear ( i i ) MOLECULE TYPE: other nucleic acid (synthetic DNA)

( x i ) SEQUENCE DESCRIPTION: SEQ ID NO:30:

ACGAATTCCC AGCTAATTCG CGTCTAC        27

( 2 ) INFORMATION FOR SEQ ID NO:31:

( i ) SEQUENCE CHARACTERISTICS:
( A ) LENGTH: 58
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:31:

```
Val Asp Asn Lys Phe Asn Lys Glu Gln Gln Asn Ala Phe Tyr Glu
  1               5                  10                  15

Ile Leu His Leu Pro Asn Leu Asn Glu Glu Gln Arg Asn Ala Phe
                 20                  25                  30

Ile Gln Ser Leu Lys Asp Asp Pro Ser Gln Ser Ala Asn Leu Leu
                 35                       40                  45

Ala Glu Ala Lys Lys Leu Asn Asp Ala Gln Ala Pro Lys
                 50                       55
```

( 2 ) INFORMATION FOR SEQ ID NO:32:

( i ) SEQUENCE CHARACTERISTICS:
( A ) LENGTH: 25
( B ) TYPE: nucleic acid
( C ) STRANDEDNESS: single
( D ) TOPOLOGY: linear ( i i ) MOLECULE TYPE: other nucleic acid (synthetic DNA)

( x i ) SEQUENCE DESCRIPTION: SEQ ID NO:32:

GAGTCGACTC CATTCGTTTG TGAAT        25

( 2 ) INFORMATION FOR SEQ ID NO:33:

( i ) SEQUENCE CHARACTERISTICS:
( A ) LENGTH: 30
( B ) TYPE: nucleic acid
( C ) STRANDEDNESS: single
( D ) TOPOLOGY: linear ( i i ) MOLECULE TYPE: other nucleic acid (synthetic DNA)

( x i ) SEQUENCE DESCRIPTION: SEQ ID NO:33:

CTGTCGACAG CTAGCACCCA AAAGAACTGG        30

( 2 ) INFORMATION FOR SEQ ID NO:34:

( i ) SEQUENCE CHARACTERISTICS:
( A ) LENGTH: 1300
( B ) TYPE: nucleic acid
( C ) STRANDEDNESS: double
( D ) TOPOLOGY: linear ( x i ) SEQUENCE DESCRIPTION: SEQ ID NO:34:

```
AAGCTTGCAT GCAAATTCTA TTTCAAGGAG ACAGTCATA                       39
                                          ATG AAA TAC CTA TTG   54
```

5,684,146

41

-continued

42

```
                                          Met Lys Tyr Leu Leu
                                           1               5
CCT ACG GCA GCC GCT GGA TTG TTA TTA CTC GCT GCC CAA CCA GCG        99
Pro Thr Ala Ala Ala Gly Leu Leu Leu Leu Ala Ala Gln Pro Ala
                10                  15                  20

ATG GCC CAG GTG CAG CTG CAG GAG TCT GGA GGA GGC CTG GTA CAG       144
Met Ala Gln Val Gln Leu Gln Glu Ser Gly Gly Gly Leu Val Gln
                    25                  30                  35

CCT GGG GGT TCT CTG AGA CTC TCC TGT GGA ACT TCT GGA TTC ACC       189
Pro Gly Gly Ser Leu Arg Leu Ser Cys Gly Thr Ser Gly Phe Thr
                40                  45                  50

CTC ACT GAT GAC TAC ATG ACC TGG GTC CGC CAG CCT CCA GGA AAG       234
Leu Thr Asp Asp Tyr Met Thr Trp Val Arg Gln Pro Pro Gly Lys
                    55                  60                  65

GCA CTT GAG TGG TTG GGT TTT ATT AGA GAC AGA GCT AAT GGT TAC       279
Ala Leu Glu Trp Leu Gly Phe Ile Arg Asp Arg Ala Asn Gly Tyr
                70                  75                  80

ACA ACA GAG TAC AGT GCA TCT GTG AAG GGT CGG TTC ACC ATC TCC       324
Thr Thr Glu Tyr Ser Ala Ser Val Lys Gly Arg Phe Thr Ile Ser
                    85                  90                  95

AGA GAT AAT TCC CAA AGC ATC GTC TAT CTT CAA ATG AAC ACC CTG       369
Arg Asp Asn Ser Gln Ser Ile Val Tyr Leu Gln Met Asn Thr Leu
                100                 105                 110

AGA GTT GAG GAC AGT GCC ACT TAT TAC TGT GCA AGG CCC AAA GGC       414
Arg Val Glu Asp Ser Ala Thr Tyr Tyr Cys Ala Arg Pro Lys Gly
                    115                 120                 125

TAC TTT CCC TAT GCT ATG GAC TAC TGG GGT CAA GGA ACC TCA GTC       459
Tyr Phe Pro Tyr Ala Met Asp Tyr Trp Gly Gln Gly Thr Ser Val
                130                 135                 140

ATC GTC                                                           465
Ile Val

TAATAAGAGC TATCCCGGGA GCTTGCATGC AAATTCTATT TCAAGGAGAC            515

AGTCATA                                                           522

ATG AAA TAC CTA TTG CCT ACG GCA GCC GCT GGA TTG TTA TTA           564
Met Lys Tyr Leu Leu Pro Thr Ala Ala Ala Gly Leu Leu Leu
 1               5                  10

CTC GCT GCC CAA CCA GCG ATG GCC GAC ATC GAG CTC ACC CAG TCT       609
Leu Ala Ala Gln Pro Ala Met Ala Asp Ile Glu Leu Thr Gln Ser
15                  20                  25

CCT GCC TCC CAG TCT GCA TCT CTG GGA GAA AGT GTC ACC ATC ACA       654
Pro Ala Ser Gln Ser Ala Ser Leu Gly Glu Ser Val Thr Ile Thr
30                  35                  40

TGC CTG GCA AGT CAG ACC ATT GGT ACA TGG TTA GCA TGG TAT CAG       699
Cys Leu Ala Ser Gln Thr Ile Gly Thr Trp Leu Ala Trp Tyr Gln
45                  50                  55

CAG AAA CCA GGG AAA TCT CCT CAG CTC CTG ATT TAT GCT GCA ACC       744
Gln Lys Pro Gly Lys Ser Pro Gln Leu Leu Ile Tyr Ala Ala Thr
60                  65                  70

AGC TTG GCA GAT GGG GTC CCA TCA AGG TTC AGT GGT AGT GGA TCT       789
Ser Leu Ala Asp Gly Val Pro Ser Arg Phe Ser Gly Ser Gly Ser
75                  80                  85

GGC ACA AAA TTT TCC TTC AAG ATC AGC AGC CTA CAG GCT GAA GAT       834
Gly Thr Lys Phe Ser Phe Lys Ile Ser Ser Leu Gln Ala Glu Asp
90                  95                  100

TTT GTA AGT TAT TAC TGT CAA CAA CTT TAC AGT ACT CCG TGG ACG       879
Phe Val Ser Tyr Tyr Cys Gln Gln Leu Tyr Ser Thr Pro Trp Thr
105                 110                 115

TTC GGT GGA GGC ACC AAG CTG GAG TCG ACT GCG CAA CAC GAT GAA       924
Phe Gly Gly Gly Thr Lys Leu Glu Ser Thr Ala Gln His Asp Glu
```

```
                  120                        125                        130
         GCC  GTA  GAC  AAC  AAA  TTC  AAC  AAA  GAA  CAA  CAA  AAC  GCG  TTC  TAT    969
         Ala  Val  Asp  Asn  Lys  Phe  Asn  Lys  Glu  Gln  Gln  Asn  Ala  Phe  Tyr
         135                      140                      145

GAG  ATC  TTA  CAT  TTA  CCT  AAC  TTA  AAC  GAA  GAA  CAA  CGA  AAC  GCC   1014
         Glu  Ile  Leu  His  Leu  Pro  Asn  Leu  Asn  Glu  Glu  Gln  Arg  Asn  Ala
         150                      155                      160

TTC  ATC  CAA  AGT  TTA  AAA  GAT  GAC  CCA  AGC  CAA  AGC  GCT  AAC  CTT   1059
         Phe  Ile  Gln  Ser  Leu  Lys  Asp  Asp  Pro  Ser  Gln  Ser  Ala  Asn  Leu
         165                      170                      175

TTA  GCA  GAA  GCT  AAA  AAG  CTA  AAT  GAT  GCT  CAG  GCG  CCG  AAA  GTA   1104
         Leu  Ala  Glu  Ala  Lys  Lys  Leu  Asn  Asp  Ala  Gln  Ala  Pro  Lys  Val
         180                      185                      190

GAC  AAC  AAA  TTC  AAC  AAA  GAA  CAA  CAA  AAC  GCG  TTC  TAT  GAG  ATC   1149
         Asp  Asn  Lys  Phe  Asn  Lys  Glu  Gln  Gln  Asn  Ala  Phe  Tyr  Glu  Ile
         195                      200                      205

TTA  CAT  TTA  CCT  AAC  TTA  AAC  GAA  GAA  CAA  CGA  AAC  GCC  TTC  ATC   1194
         Leu  His  Leu  Pro  Asn  Leu  Asn  Glu  Glu  Gln  Arg  Asn  Ala  Phe  Ile
         210                      215                      220

CAA  AGT  TTA  AAA  GAT  GAC  CCA  AGC  CAA  AGC  GCT  AAC  CTT  TTA  GCA   1239
         Gln  Ser  Leu  Lys  Asp  Asp  Pro  Ser  Gln  Ser  Ala  Asn  Leu  Leu  Ala
         225                      230                      235

GAA  GCT  AAA  AAG  CTA  AAT  GAT  GCT  CAG  GCG  CCG  AAA  GTA  GAC  GCG   1284
         Glu  Ala  Lys  Lys  Leu  Asn  Asp  Ala  Gln  Ala  Pro  Lys  Val  Asp  Ala
         240                      245                      250

AAT  TAGCTGGGAA TTC                                                          1300
         Asn
         255
```

( 2 ) INFORMATION FOR SEQ ID NO:35:

( i ) SEQUENCE CHARACTERISTICS:
        ( A ) LENGTH: 1228
        ( B ) TYPE: nucleic acid
        ( C ) STRANDEDNESS: double
        ( D ) TOPOLOGY: linear ( x i ) SEQUENCE DESCRIPTION: SEQ ID NO:35:

```
         AAGCTTGCAT GCAAATTCTA TTTCAAGGAG ACAGTCATA                                    39

ATG  AAA  TAC  CTA  TTG                   54
                                            Met  Lys  Tyr  Leu  Leu
                                              1                    5

CCT  ACG  GCA  GCC  GCT  GGA  TTG  TTA  TTA  CTC  GCT  GCC  CAA  CCA  GCG    99
         Pro  Thr  Ala  Ala  Ala  Gly  Leu  Leu  Leu  Leu  Ala  Ala  Gln  Pro  Ala
                             10                       15                      20

ATG  GCC  CAG  GTG  CAG  CTG  CAG  GAG  TCT  GGA  GGA  GGC  CTG  GTA  CAG   144
         Met  Ala  Gln  Val  Gln  Leu  Gln  Glu  Ser  Gly  Gly  Gly  Leu  Val  Gln
                         25                      30                          35

CCT  GGG  GGT  TCT  CTG  AGA  CTC  TCC  TGT  GGA  ACT  TCT  GGA  TTC  ACC   189
         Pro  Gly  Gly  Ser  Leu  Arg  Leu  Ser  Cys  Gly  Thr  Ser  Gly  Phe  Thr
                         40                      45                          50

CTC  ACT  GAT  GAC  TAC  ATG  ACC  TGG  GTC  CGC  CAG  CCT  CCA  GGA  AAG   234
         Leu  Thr  Asp  Asp  Tyr  Met  Thr  Trp  Val  Arg  Gln  Pro  Pro  Gly  Lys
                         55                      60                          65

GCA  CTT  GAG  TGG  TTG  GGT  TTT  ATT  AGA  GAC  AGA  GCT  AAT  GGT  TAC   279
         Ala  Leu  Glu  Trp  Leu  Gly  Phe  Ile  Arg  Asp  Arg  Ala  Asn  Gly  Tyr
                         70                      75                          80

ACA  ACA  GAG  TAC  AGT  GCA  TCT  GTG  AAG  GGT  CGG  TTC  ACC  ATC  TCC   324
         Thr  Thr  Glu  Tyr  Ser  Ala  Ser  Val  Lys  Gly  Arg  Phe  Thr  Ile  Ser
                         85                      90                          95

AGA  GAT  AAT  TCC  CAA  AGC  ATC  GTC  TAT  CTT  CAA  ATG  AAC  ACC  CTG   369
```

```
              Arg Asp Asn Ser Gln Ser Ile Val Tyr Leu Gln Met Asn Thr Leu
                              100                 105                 110

AGA GTT GAG GAC AGT GCC ACT TAT TAC TGT GCA AGG CCC AAA GGC                  414
Arg Val Glu Asp Ser Ala Thr Tyr Tyr Cys Ala Arg Pro Lys Gly
            115                 120                 125

TAC TTT CCC TAT GCT ATG GAC TAC TGG GGT CAA GGA ACC TCA GTC                  459
Tyr Phe Pro Tyr Ala Met Asp Tyr Trp Gly Gln Gly Thr Ser Val
            130                 135                 140

ATC GTC TCC TCA GGT GGC GGT GGA TCC GGC GGT GGT GGG TCG GGT                  504
Ile Val Ser Ser Gly Gly Gly Gly Ser Gly Gly Gly Gly Ser Gly
            145                 150                 155

GGC GGC GGA TCT GAC ATC GAG CTC ACC CAG TCT CCT GCC TCC CAG                  549
Gly Gly Gly Ser Asp Ile Glu Leu Thr Gln Ser Pro Ala Ser Gln
            160                 165                 170

TCT GCA TCT CTG GGA GAA AGT GTC ACC ATC ACA TGC CTG GCA AGT                  594
Ser Ala Ser Leu Gly Glu Ser Val Thr Ile Thr Cys Leu Ala Ser
            175                 180                 185

CAG ACC ATT GGT ACA TGG TTA GCA TGG TAT CAG CAG AAA CCA GGG                  639
Gln Thr Ile Gly Thr Trp Leu Ala Trp Tyr Gln Gln Lys Pro Gly
            190                 195                 200

AAA TCT CCT CAG CTC CTG ATT TAT GCT GCA ACC AGC TTG GCA GAT                  684
Lys Ser Pro Gln Leu Leu Ile Tyr Ala Ala Thr Ser Leu Ala Asp
            205                 210                 215

GGG GTC CCA TCA AGG TTC AGT GGT AGT GGA TCT GGC ACA AAA TTT                  729
Gly Val Pro Ser Arg Phe Ser Gly Ser Gly Ser Gly Thr Lys Phe
            220                 225                 230

TCC TTC AAG ATC AGC AGC CTA CAG GCT GAA GAT TTT GTA AGT TAT                  774
Ser Phe Lys Ile Ser Ser Leu Gln Ala Glu Asp Phe Val Ser Tyr
            235                 240                 245

TAC TGT CAA CAA CTT TAC AGT ACT CCG TGG ACG TTC GGT GGA GGC                  819
Tyr Cys Gln Gln Leu Tyr Ser Thr Pro Trp Thr Phe Gly Gly Gly
            250                 255                 260

ACC AAG CTG GAG TCG ACT GCG CAA CAC GAT GAA GCC GTA GAC AAC                  864
Thr Lys Leu Glu Ser Thr Ala Gln His Asp Glu Ala Val Asp Asn
            265                 270                 275

AAA TTC AAC AAA GAA CAA CAA AAC GCG TTC TAT GAG ATC TTA CAT                  909
Lys Phe Asn Lys Glu Gln Gln Asn Ala Phe Tyr Glu Ile Leu His
            280                 285                 290

TTA CCT AAC TTA AAC GAA GAA CAA CGA AAC GCC TTC ATC CAA AGT                  954
Leu Pro Asn Leu Asn Glu Glu Gln Arg Asn Ala Phe Ile Gln Ser
            295                 300                 305

TTA AAA GAT GAC CCA AGC CAA AGC GCT AAC CTT TTA GCA GAA GCT                  999
Leu Lys Asp Asp Pro Ser Gln Ser Ala Asn Leu Leu Ala Glu Ala
            310                 315                 320

AAA AAG CTA AAT GAT GCT CAG GCG CCG AAA GTA GAC AAC AAA TTC                 1044
Lys Lys Leu Asn Asp Ala Gln Ala Pro Lys Val Asp Asn Lys Phe
            325                 330                 335

AAC AAA GAA CAA CAA AAC GCG TTC TAT GAG ATC TTA CAT TTA CCT                 1089
Asn Lys Glu Gln Gln Asn Ala Phe Tyr Glu Ile Leu His Leu Pro
            340                 345                 350

AAC TTA AAC GAA GAA CAA CGA AAC GCC TTC ATC CAA AGT TTA AAA                 1134
Asn Leu Asn Glu Glu Gln Arg Asn Ala Phe Ile Gln Ser Leu Lys
            355                 360                 365

GAT GAC CCA AGC CAA AGC GCT AAC CTT TTA GCA GAA GCT AAA AAG                 1179
Asp Asp Pro Ser Gln Ser Ala Asn Leu Leu Ala Glu Ala Lys Lys
            370                 375                 380

CTA AAT GAT GCT CAG GCG CCG AAA GTA GAC GCG AAT TAGCTGGGAA                  1225
Leu Asn Asp Ala Gln Ala Pro Lys Val Asp Ala Asn
            385                 390

TTC                                                                         1228
```

( 2 ) INFORMATION FOR SEQ ID NO:36:

( i ) SEQUENCE CHARACTERISTICS:
      ( A ) LENGTH: 1288
      ( B ) TYPE: nucleic acid
      ( C ) STRANDEDNESS: double
      ( D ) TOPOLOGY: linear ( x i ) SEQUENCE DESCRIPTION: SEQ ID NO:36:

```
AAGCTTGCAT GCAAATTCTA TTTCAAGGAG ACAGTCATAA TGAAATACCT ATTGCCTACG     60
GCAGCCGCTG GATTGTTATT ACTCGCTGCC CAACCAGCGA TGGCCCAGGT GCAGCTGCAG    120
GAGTCAGGAC CTGGCCTGGT GGCGCCCTCA CAGAGCCTGT CCATCACATG CACCGTCTCA    180
GGGTTCTCAT TAACCGGCTA TGGTGTAAAC TGGGTTCGCC AGCCTCCAGG AAAGGGTCTG    240
GAGTGGCTGG GAATGATTTG GGGTGATGGA AACACAGACT ATAATTCAGC TCTCAAATCC    300
AGACTGAGCA TCAGCAAGGA CAACTCCAAG AGCCAAGTTT TCTTAAAAAT GAACAGTCTG    360
CACACTGATG ACACAGCCAG GTACTACTGT GCCAGAGAGA GAGATTATAG GCTTGACTAC    420
TGGGGCCAAG GCACCACGGT CACCGTCTCC TCATAATAAG AGCTATCCCG GGAGCTTGCA    480
TGCAAATTCT ATTTCAAGGA GACAGTCATA ATGAAATACC TATTGCCTAC GGCAGCCGCT    540
GGATTGTTAT TACTCGCTGC CCAACCAGCG ATGGCCGACA TCGAGCTCAC CCAGTCTCCA    600
GCCTCCCTTT CTGCGTCTGT GGGAGAAACT GTCACCATCA CATGTCGAGC AAGTGGGAAT    660
ATTCACAATT ATTTAGCATG GTATCAGCAG AAACAGGGAA AATCTCCTCA GCTCCTGGTC    720
TATTATACAA CAACCTTAGC AGATGGTGTG CCATCAAGGT TCAGTGGCAG TGGATCAGGA    780
ACACAATATT CTCTCAAGAT CAACAGCCTG CAACCTGAAG ATTTTGGGAG TTATTACTGT    840
CAACATTTTT GGAGTACTCC TCGGACGTTC GGTGGAGGCA CCAAGCTGGA GTCGACTGCG    900
CAACACGATG AAGCCGTAGA CAACAAATTC AACAAAGAAC AACAAAACGC GTTCTATGAG    960
ATCTTACATT TACCTAACTT AAACGAAGAA CAACGAAACG CCTTCATCCA AAGTTTAAAA   1020
GATGACCCAA GCCAAAGCGC TAACCTTTTA GCAGAAGCTA AAAAGCTAAA TGATGCTCAG   1080
GCGCCGAAAG TAGACAACAA ATTCAACAAA GAACAACAAA ACGCGTTCTA TGAGATCTTA   1140
CATTTACCTA ACTTAAACGA AGAACAACGA AACGCCTTCA TCCAAAGTTT AAAAGATGAC   1200
CCAAGCCAAA GCGCTAACCT TTTAGCAGAA GCTAAAAAGC TAAATGATGC TCAGGCGCCG   1260
AAAGTAGACG CGAATTAGCT GGGAATTC                                      1288
```